(12) United States Patent
Lee et al.

(10) Patent No.: US 12,171,582 B2
(45) Date of Patent: Dec. 24, 2024

(54) BIOSIGNAL SENSOR AND SENSOR SYSTEM AND ELECTRONIC DEVICE

(71) Applicant: Samsung Electronics Co., Ltd., Suwon-si (KR)

(72) Inventors: Gae Hwang Lee, Seongnam-si (KR); Youngjun Yun, Seongnam-si (KR); Hyun Bum Kang, Yongin-si (KR); Yeongjun Lee, Seongnam-si (KR); Jong Won Chung, Hwaseong-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 355 days.

(21) Appl. No.: 17/510,728

(22) Filed: Oct. 26, 2021

(65) Prior Publication Data

US 2022/0240862 A1    Aug. 4, 2022

(30) Foreign Application Priority Data

Feb. 2, 2021   (KR) ........................ 10-2021-0014777

(51) Int. Cl.
    *A61B 5/00*     (2006.01)
    *A61B 5/024*     (2006.01)
    *G02B 27/28*     (2006.01)

(52) U.S. Cl.
    CPC .......... *A61B 5/721* (2013.01); *A61B 5/02416* (2013.01); *A61B 5/02438* (2013.01); *G02B 27/286* (2013.01)

(58) Field of Classification Search
CPC .... G02B 27/287; G02B 27/286; A61B 5/721; A61B 5/02438; A61B 5/02108; A61B 2562/0233
See application file for complete search history.

(56) References Cited

U.S. PATENT DOCUMENTS

| | | |
|---|---|---|
| 8,525,992 B2 | 9/2013 | Shin et al. |
| 9,872,627 B2 | 1/2018 | Lee |
| 9,970,955 B1 | 5/2018 | Homyk et al. |

(Continued)

FOREIGN PATENT DOCUMENTS

| | | |
|---|---|---|
| KR | 101050694 B1 | 7/2011 |
| KR | 10-2016-0101447 A | 8/2016 |

(Continued)

*Primary Examiner* — Christopher Koharski
*Assistant Examiner* — Felix A Donis-Barrera
(74) *Attorney, Agent, or Firm* — HARNESS, DICKEY & PIERCE, P.L.C.

(57) ABSTRACT

A biosignal sensor includes a light-emitting element, a photo-detective element configured to detect a biosignal from light reflected from an in-vivo target, a first polarizer configured to selectively transmit light in a first polarization direction, and a second polarizer configured to selectively transmit light in a second polarization direction. The light-emitting element includes a first light-emitting element overlapped with the first polarizer in a vertical direction, the photo-detective element includes a first photo-detective element overlapped with the second polarizer in the vertical direction, the first light-emitting element and the first photo-detective element are parallel to each other along a first direction that is perpendicular to the vertical direction, and the first polarization direction and the second polarization direction are perpendicular to each other.

26 Claims, 21 Drawing Sheets

(56) References Cited

U.S. PATENT DOCUMENTS

| | | |
|---|---|---|
| 10,466,100 B2 | 11/2019 | Cho et al. |
| 10,883,874 B2 | 1/2021 | Cho et al. |
| 2011/0085163 A1* | 4/2011 | Shin |
| 2016/0238447 A1* | 8/2016 | Cho |
| 2018/0325397 A1* | 11/2018 | Presura .............. A61B 5/02255 |
| 2018/0325427 A1 | 11/2018 | Itoh et al. |
| 2020/0170522 A1* | 6/2020 | Kim ........................ G06F 1/163 |
| 2021/0007617 A1* | 1/2021 | Kim .................... A61B 5/0295 |
| 2021/0113137 A1* | 4/2021 | Soli ........................ G06F 3/016 |

FOREIGN PATENT DOCUMENTS

| | | | |
|---|---|---|---|
| KR | 101830188 B1 | 2/2018 | |
| KR | 10-2019-0119382 A | 10/2019 | |
| WO | WO-2014077405 A1 * | 5/2014 | ......... G02B 26/0833 |

\* cited by examiner

BIOSIGNAL SENSOR AND SENSOR SYSTEM AND ELECTRONIC DEVICE

CROSS-REFERENCE TO RELATED APPLICATION

This application claims priority to and the benefit of, under 35 U.S.C. § 119, Korean Patent Application No. 10-2021-0014777 filed in the Korean Intellectual Property Office on Feb. 2, 2021, the entire contents of which are incorporated herein by reference.

BACKGROUND

1. Field

A biosignal sensor, a sensor system, and an electronic device are disclosed.

2. Description of the Related Art

In recent years, research on electronic devices for obtaining biometric information by adhering to or attaching to the skin is being conducted. Such electronic devices include a biosignal sensor for obtaining biometric information. For example, a photoplethysmography (PPG) sensor may obtain a PPG signal from a user, and by analyzing the PPG signal, biometric information such as a user's blood pressure, arrhythmia, heart rate, and/or oxygen saturation may be obtained.

SUMMARY

Some example embodiments provide a biosignal sensor capable of improving performance by reducing noise caused by a change in position between a skin and a biosignal sensor due to a user's motion.

Some example embodiments provide a sensor system including the biosignal sensor.

Some example embodiments provide an electronic device including the biosignal sensor or the sensor system.

According to some example embodiments, a biosignal sensor may include a light-emitting element, a photo-detective element configured to detect a biosignal from light reflected from a target that is external to the biosignal sensor, a first polarizer configured to selectively transmit light in a first polarization direction, and a second polarizer configured to selectively transmit light in a second polarization direction, wherein the light-emitting element includes a first light-emitting element overlapped with the first polarizer in a vertical direction. The photo-detective element may include a first photo-detective element overlapped with the second polarizer in the vertical direction, the first light-emitting element and the first photo-detective element may be arranged to be parallel to each other along a first direction that is perpendicular to the vertical direction, and the first polarization direction and the second polarization direction may be perpendicular to each other.

An angle of the first polarization direction or the second polarization direction with respect to the first direction may satisfy Relationship Equation 1.

$$2S_1/S_0 < 1.0 \quad \text{[Relationship Equation 1]}$$

In Relationship Equation 1, $S_1$ is an amount of light measured by the first photo-detective element when the angle of the first polarization direction or the second polarization direction with respect to the first direction is θ degrees, and $S_0$ is an amount of light measured by the first photo-detective element when the light measured by the first photo-detective element is not polarized in at least the second polarization direction.

The angle of the first polarization direction or the second polarization direction with respect to the first direction may be in a range of about −8.5 degrees to about +8.5 degrees.

The first polarization direction or the second polarization direction may be parallel to the first direction.

One of the first polarization direction or the second polarization direction may be parallel to the first direction, and another of the first polarization direction or the second polarization direction may be perpendicular to the first direction.

The first photo-detective element may be in plural, such that the photo-detective element includes a plurality of first photo-detective elements, the plurality of first photo-detective elements including the first photo-detective element, wherein at least some first photo-detective elements of the plurality of first photo-detective elements are at opposite sides of the first light-emitting element along the first direction.

Some other first photo-detective elements of the plurality of first photo-detective elements may be at opposite sides of the first light-emitting element along a second direction that is perpendicular to both the first direction and the vertical direction.

The photo-detective element may further include a second photo-detective element, the second photo-detective element being not overlapped with the second polarizer in the vertical direction.

The first light-emitting element and the second photo-detective element may be parallel to each other along a third direction, the third direction being not parallel or perpendicular to the first direction.

The light-emitting element may further include a second light-emitting element, the second light-emitting element being not overlapped with the first polarizer in the vertical direction.

The first photo-detective element and the second photo-detective element are in plural, respectively, such that the photo-detective element includes a plurality of first photo-detective elements, the plurality of first photo-detective elements including the first photo-detective element, and the photo-detective element includes a plurality of second photo-detective elements, the plurality of second photo-detective elements including the second photo-detective element, wherein some first photo-detective elements of the plurality of first photo-detective elements are at one or opposite sides of the first light-emitting element along the first direction, some other first photo-detective elements of the plurality of first photo-detective elements are at one or opposite sides of the first light-emitting element along a second direction that is perpendicular to the first direction and the vertical direction, some second photo-detective elements of the plurality of second photo-detective elements are at one or opposite sides of the first light-emitting element along a third direction, the third direction being different from the first direction and the second direction and perpendicular to the vertical direction, and some other second photo-detective elements of the plurality of second photo-detective elements are at one or opposite sides of the first light-emitting element along a fourth direction, the fourth direction being different from the first direction, the second direction, and the third direction and perpendicular to the vertical direction.

The biosignal sensor may further include a phase retarder between the first light-emitting element and the first polarizer.

The biosignal sensor may be a skin-attachable photoplethysmography (PPG) sensor.

According to some example embodiments, a biosignal sensor may include a first biosignal sensor including a first photo-detective element and a polarizer that is overlapped with the first photo-detective element in a vertical direction, and a second biosignal sensor including a second photo-detective element that does not overlap with any polarizers in the vertical direction, wherein the first biosignal sensor and the second biosignal sensor are configured to operate independently.

The biosignal sensor may further include a first light-emitting element that is overlapped with a separate polarizer in the vertical direction.

The first biosignal sensor may be in plural, such that the biosignal sensor includes a plurality of first biosignal sensors, the plurality of first biosignal sensors including the first biosignal sensor, wherein some first biosignal sensors of the plurality of first biosignal sensors are at one or opposite sides of the first light-emitting element along a first direction that is perpendicular to the vertical direction, and some other first biosignal sensors of the plurality of first biosignal sensors are at one or opposite sides of the first light-emitting element along a second direction, the second direction being perpendicular to both the first direction and the vertical direction.

The second biosignal sensor may be in plural such that the biosignal sensor includes a plurality of second biosignal sensors, the plurality of second biosignal sensors including the second biosignal sensor, wherein some second biosignal sensors of the plurality of the second biosignal sensors are at one or opposite sides of the first light-emitting element along a third direction, the third direction being different from both the first direction and the second direction and perpendicular to the vertical direction and some other second biosignal sensors of the plurality of the second biosignal sensors are at one or opposite sides of the first light-emitting element along a fourth direction, the fourth direction being different from the first direction, the second direction, and the third direction and perpendicular to the vertical direction.

The biosignal sensor may further include a light-emitting element.

The light-emitting element may include a first light-emitting element provided with a polarizer.

The first biosignal sensor may further include a first light-emitting element that is overlapped with a separate polarizer in the vertical direction, and the second biosignal sensor may further include a second light-emitting element that does not overlap with any polarizers in the vertical direction.

The first biosignal sensor may further include a phase retarder.

Each of the first biosignal sensor and the second biosignal sensor may be a skin-attachable photoplethysmography (PPG) sensor.

According to some example embodiments, a sensor system including the biosignal sensor is provided.

The sensor system may further include a motion detecting sensor.

According to some example embodiments, an electronic device including the biosignal sensor or the sensor system is provided.

According to some example embodiments, as a method of operating the biosignal sensor, a method of operating a sensor system includes detecting a motion of an attachment or wearing portion of a user, selectively driving the first biosignal sensor or the second biosignal sensor according to the detected motion, and obtaining a biosignal from the first biosignal sensor or the second biosignal sensor.

The selectively driving of the first biosignal sensor or the second biosignal sensor may include selectively driving the first biosignal sensor in response to the motion of the attachment or wearing portion of the user being detected, and selectively driving the second biosignal sensor in response to the motion of the attachment or wearing portion of the user not being detected.

It is possible to improve performance by reducing noise caused by a change in a position between the skin and the biosignal sensor due to motion.

DETAILED DESCRIPTION

Figure 1:
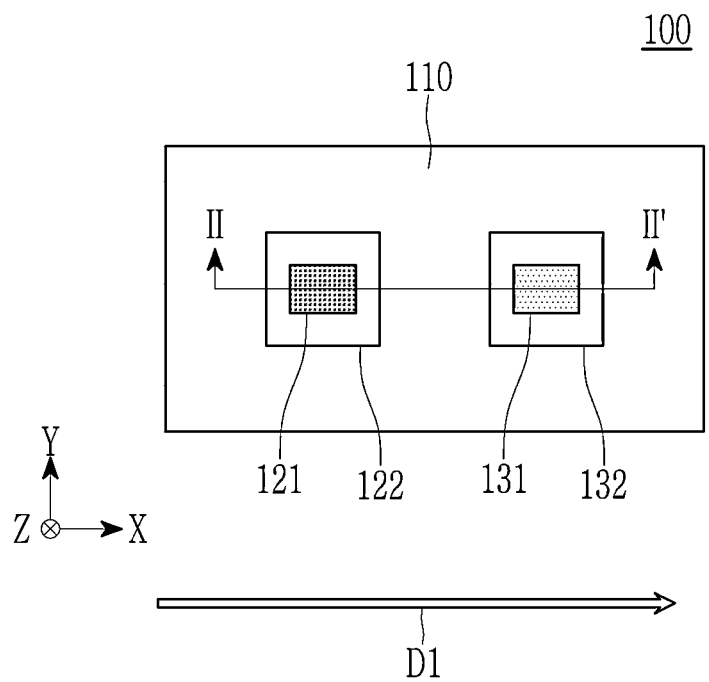
FIG. 1 is a plan view showing an example of a biosignal sensor according to some example embodiments.

Hereinafter, some example embodiments are described in detail so that those of ordinary skill in the art can easily implement them. However, the structures that are actually applied may be implemented in various different forms, and is not limited to the example embodiments described herein.

In the drawings, the thickness of layers, films, panels, regions, etc., are exaggerated for clarity. It will be understood that when an element such as a layer, film, region, or substrate is referred to as being "on" another element, it may be directly on the other element or intervening elements may also be present. In contrast, when an element is referred to as being "directly on" another element, there are no intervening elements present.

It will further be understood that when an element is referred to as being "on" another element, it may be above or beneath or adjacent (e.g., horizontally adjacent) to the other element.

It will be understood that elements and/or properties thereof (e.g., structures, surfaces, directions, or the like), which may be referred to as being "perpendicular," "parallel," "coplanar," or the like with regard to other elements and/or properties thereof (e.g., structures, surfaces, directions, or the like) may be "perpendicular," "parallel," "coplanar," or the like or may be "substantially perpendicular," "substantially parallel," "substantially coplanar," respectively, with regard to the other elements and/or properties thereof.

Elements and/or properties thereof (e.g., structures, surfaces, directions, or the like) that are "substantially perpendicular" with regard to other elements and/or properties thereof will be understood to be "perpendicular" with regard to the other elements and/or properties thereof within manufacturing tolerances and/or material tolerances and/or have a deviation in magnitude and/or angle from "perpendicular," or the like with regard to the other elements and/or properties thereof that is equal to or less than 10% (e.g., a. tolerance of ±10%).

Elements and/or properties thereof (e.g., structures, surfaces, directions, or the like) that are "substantially parallel" with regard to other elements and/or properties thereof will be understood to be "parallel" with regard to the other elements and/or properties thereof within manufacturing tolerances and/or material tolerances and/or have a deviation in magnitude and/or angle from "parallel," or the like with regard to the other elements and/or properties thereof that is equal to or less than 10% (e.g., a. tolerance of ±10%).

Elements and/or properties thereof (e.g., structures, surfaces, directions, or the like) that are "substantially coplanar" with regard to other elements and/or properties thereof will be understood to be "coplanar" with regard to the other elements and/or properties thereof within manufacturing tolerances and/or material tolerances and/or have a deviation in magnitude and/or angle from "coplanar," or the like with regard to the other elements and/or properties thereof that is equal to or less than 10% (e.g., a. tolerance of ±10%).

It will be understood that elements and/or properties thereof may be recited herein as being "the same" or "equal" as other elements, and it will be further understood that elements and/or properties thereof recited herein as being "identical" to, "the same" as, or "equal" to other elements may be "identical" to, "the same" as, or "equal" to or "substantially identical" to, "substantially the same" as or "substantially equal" to the other elements and/or properties thereof. Elements and/or properties thereof that are "substantially identical" to, "substantially the same" as or "substantially equal" to other elements and/or properties thereof will be understood to include elements and/or properties thereof that are identical to, the same as, or equal to the other elements and/or properties thereof within manufacturing tolerances and/or material tolerances. Elements and/or properties thereof that are identical or substantially identical to and/or the same or substantially the same as other elements and/or properties thereof may be structurally the same or substantially the same, functionally the same or substantially the same, and/or compositionally the same or substantially the same.

It will be understood that elements and/or properties thereof described herein as being the "substantially" the same and/or identical encompasses elements and/or properties thereof that have a relative difference in magnitude that is equal to or less than 10%. Further, regardless of whether elements and/or properties thereof are modified as "substantially," it will be understood that these elements and/or properties thereof should be construed as including a manufacturing or operational tolerance (e.g., ±10%) around the stated elements and/or properties thereof.

When the terms "about" or "substantially" are used in this specification in connection with a numerical value, it is intended that the associated numerical value include a tolerance of ±10% around the stated numerical value. When ranges are specified, the range includes all values therebetween such as increments of 0.1%.

As used herein, "substantially" includes an approximate range taking into account variations and errors within a normal range, for example, about ±5%, ±4%, ±3%, ±2%, or ±1%.

Hereinafter, a biosignal sensor according to some example embodiments is described.

The biosignal sensor is a sensor capable of detecting a biosignal temporarily or in real time. The biosignal may be, for example, a blood flow rate, a change in oxygen distribution, and/or an electrocardiogram obtained from an in-vivo target such as a blood vessel, but is not limited thereto.

The biosignal sensor includes a light-emitting element configured to emit light to a living body and a photo-detective element configured to detect a biosignal from light reflected from an in-vivo target such as a blood vessel.

Figure 2:
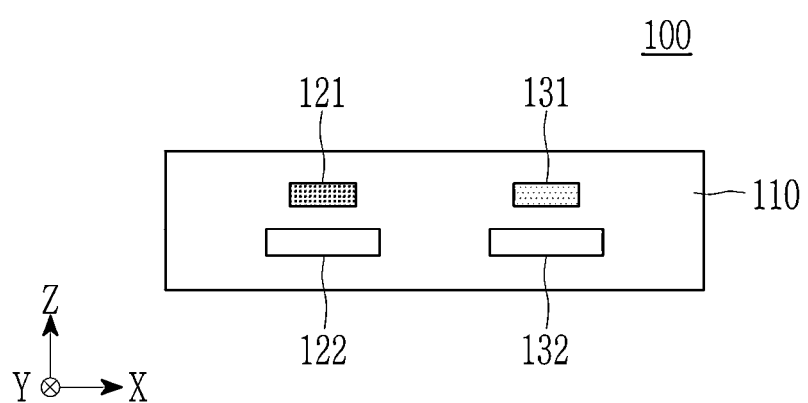
FIG. 2 is a cross-sectional view of an example of the biosignal sensor of FIG. 1 taken along line II-II'.

FIG. 1 is a plan view showing an example of a biosignal sensor according to some example embodiments, and FIG. 2 is a cross-sectional view showing an example of the biosignal sensor of FIG. 1 taken along line II-II'.

Referring to FIGS. 1 and 2, the biosignal sensor 100 according to some example embodiments includes a light-transmitting layer 110, a first light-emitting element 121, a first polarizer 122, a first photo-detective element 131, and a second polarizer 132.

The light-transmitting layer 110 may support or surround the first light-emitting element 121, the first polarizer 122, the first photo-detective element 131, and the second polarizer 132. The light-transmitting layer 110 may be, for example, a support substrate or may be formed on a separate support substrate (not shown).

The light-transmitting layer 110 may be configured to transmit light, and may have for example, light transmittance of greater than or equal to about 70%, greater than or equal to about 75%, greater than or equal to about 80%, greater than or equal to about 85%, greater than or equal to about 90%, greater than or equal to about 95%, greater than or equal to about 97%, greater than or equal to about 98%, or greater than or equal to about 99%. Accordingly, the light-transmitting layer 110 may be configured to effectively transmit light emitted from the first light-emitting element 121 and light reflected from a target that is external to the biosignal sensor 100, for example an in-vivo target (e.g., blood vessel).

In the drawing, as an example, a structure in which the first light-emitting element 121, the first polarizer 122, the first photo-detective element 131, and the second polarizer 132 are embedded in the light-transmitting layer 110 is shown. However, the first light-emitting element 121 and the first photo-detective element 131 are not limited to the structure, and may be disposed on the light-transmitting layer 110. In this case, the light-transmitting layer 110 may be disposed in a direction in which light is emitted from the first light-emitting element 121 and in a direction in which light is flowed into the first photo-detective element 131. For example, the light-transmitting layer 110 may be disposed closer to a skin and in-vivo target (e.g., blood vessel) than the first light-emitting element 121 and the first photo-detective element 131.

The light-transmitting layer 110 may be a stretchable light-transmitting layer, and the stretchable light-transmitting layer may respond flexibly to external forces or external motions such as twisting, pressing, and pulling, and may be easily restored to its original state. The light-transmitting layer 110 may include a stretchable material such as an elastomer, and the stretchable material may include an organic elastomer, an organic-inorganic elastomer, an inorganic elastomer-like material, or any combination thereof. The organic elastomer or the organic-inorganic elastomer may be, for example, substituted or unsubstituted polyorganosiloxane such as polydimethylsiloxane, an elastomer including substituted or unsubstituted butadiene moiety such as styrene-ethylene-butylene-styrene, an elastomer including a urethane moiety, an elastomer including an acrylic moiety, an elastomer including an olefin moiety, or any combination thereof, but is not limited thereto. The inorganic elastomer-like material may include an elastic ceramic, solid metal, liquid metal, or any combination thereof, but is not limited thereto.

The light-transmitting layer 110 may be one layer or two or more layers.

The first light-emitting element 121 and the first photo-detective element 131 are disposed at a particular (or, alternatively, predetermined) interval inside or above the light-transmitting layer 110, and may be parallel to each other along the first direction D1 (e.g., X direction). For example, the first light-emitting element 121 and the first photo-detective element 131 may overlap each other in the first direction D1 (e.g., X direction) that may be perpendicular to a vertical direction in which the first light-emitting element 121 and the first polarizer 122 overlap and in which the first photo-detective element 131 and the second polarizer 132 overlap. The first direction D1 may be parallel to one or both of the opposite, top and bottom surfaces of the light-transmitting layer 110.

The first light-emitting element 121 may be configured to emit light in a particular (or, alternatively, predetermined) wavelength region, and may include, for example, an inorganic light-emitting diode, an organic light-emitting diode (OLED), an organic-inorganic light-emitting diode, or a micro light-emitting diode. The first light-emitting element 121 may include, for example, a pair of electrodes and a light-emitting layer between the pair of electrodes. For example, one of the pair of electrodes may be a light-transmitting electrode and the other may be a reflecting electrode, for example, an electrode disposed close to the first polarizer 122 may be a light-transmitting electrode. For example, at least one of the pair of electrodes may be stretchable electrodes, and the stretchable electrodes may include, for example, a stretchable conductor, or may have a stretchable shape such as a wavy, wrinkled, pop-up, or non-planar mesh shape. For example, the light-emitting layer may include a light-emitter such as an organic light-emitting material, an inorganic light-emitting material, a quantum dot, and/or perovskite, but is not limited thereto. The light-emitting layer may be configured to emit light in at least a portion of a visible wavelength region to an infrared wavelength region, for example light in any one of a blue wavelength region, a green wavelength region, a red wavelength region, or an infrared wavelength region, for example light in any one of a green wavelength region, a red wavelength region, or an infrared wavelength region, for example light in a green wavelength region. The pair of electrodes may be stretchable electrodes, and the light-emitting layer may be a stretchable light-emitting layer, and accordingly, the first light-emitting element 121 may be, for example, a stretchable element.

The first photo-detective element 131 may be configured to absorb light in a particular (or, alternatively, predetermined) wavelength region and photoelectrically convert the absorbed light, and may include, for example, an inorganic photodiode or an organic photoelectric conversion element. The first photo-detective element 131 may include, for example, a pair of electrodes and a photoelectric conversion layer between the electrodes. For example, one of the pair of electrodes may be a light-transmitting electrode and the other may be a reflecting electrode, for example, an electrode disposed close to the second polarizer 132 may be a light-transmitting electrode. For example, at least one of the pair of electrodes may be stretchable electrodes, and the stretchable electrodes may include, for example, a stretchable conductor, or may have a stretchable shape such as a wavy, wrinkled, pop-up, or non-planar mesh shape. As an example, the photoelectric conversion layer may include, for example, an inorganic semiconductor, an organic semiconductor, and/or an organic-inorganic semiconductor, and may include, for example, a p-type semiconductor and an n-type semiconductor forming a pn junction. As an example, the photoelectric conversion layer may be a stretchable photoelectric conversion layer. The first photo-detective element 131 may be, for example, a stretchable element. The light emitted from the first light-emitting element 121 may pass through the light-transmitting layer 110 and be scattered and reflected by an in-vivo target such as a blood vessel, and the scattered and reflected light may pass through the light-transmitting layer 110 again and be absorbed and photoelectrically converted in the first photo-detective element 131 to obtain a biosignal. The first photo-detective element 131 may be configured to detect a biosignal from light reflected from a target that is external to the biosignal sensor 100, for example the in-vivo target.

The first polarizer 122 may be in a path through which the light emitted from the first light-emitting element 121 passes, and may be, for example, overlapped with the first light-emitting element 121 in the thickness direction (e.g., Z direction, also referred to herein as a vertical direction) of the light-transmitting layer 110 (e.g., as shown in FIG. 2, the vertical direction may be a direction extending perpendicular to one or both of opposite, top and bottom surfaces of the light-transmitting layer 110, and intersecting both the first light-emitting element 121 and the first polarizer 122). In the drawing, an example in which the first polarizer 122 is embedded in the light-transmitting layer 110 with a particular (or, alternatively, predetermined) interval from the first light-emitting element 121 is illustrated, but the present inventive concepts are not limited thereto, and the first polarizer 122 may be attached to one surface of the first light-emitting element 121.

The first polarizer 122 may linearly polarize the light emitted from the first light-emitting element 121. In other words, the first polarizer 122 may be configured to selectively transmit light of one direction (hereinafter, referred to as a "first polarization direction") out of the unpolarized light emitted from the first light-emitting element 121 that is incident on the first polarizer 122 but block and/or absorb the other light excluding the light of the first polarization direction out of the unpolarized light emitted from the first light-emitting element 121 that is incident on the first polarizer 122. Accordingly, the light passing the first polarizer 122 may be linearly polarized in the first polarization direction.

The second polarizer 132 may be in a path through which light enters the first photo-detective element 131, for example, overlapped with the first photo-detective element 131 in the thickness direction (e.g., Z direction, also referred to herein as the vertical direction) of the light-transmitting layer 110. In the drawing, the second polarizer 132 with a particular (or, alternatively, predetermined) interval from the first photo-detective element 131 is embedded in the light-transmitting layer 110 but not limited thereto and may be attached to one surface of the first photo-detective element 131.

The second polarizer 132 may linearly polarize the light flowing into the first photo-detective element 131 in advance. In other words, the second polarizer 132 may be configured to selectively transmit light of one direction (hereinafter, referred to as a "second polarization direction") out of the light entering the first photo-detective element 131 (e.g., out of the light that is incident on the second polarizer 132) but block or absorb the other light except for the light of the second polarization direction out of the light that is incident on the second polarizer 132). Accordingly, the light flowing in the first photo-detective element 131 through the second polarizer 132 may be linearly polarized in the second polarization direction. The first polarization direction and the second polarization direction may be perpendicular or substantially perpendicular to each other.

Figure 3A:
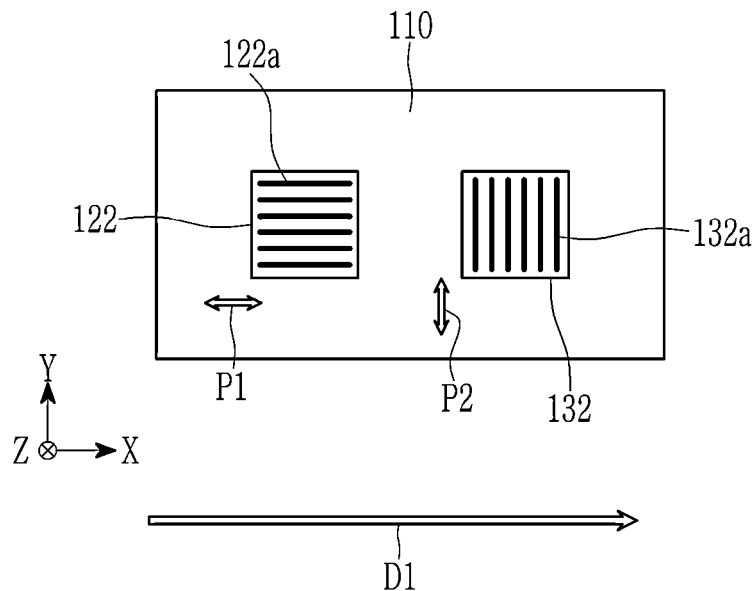
FIGS. 3A and 3B are schematic views illustrating polarization of a first polarizer and a second polarizer in the biosignal sensor of FIGS. 1 and 2.
Figure 3B:
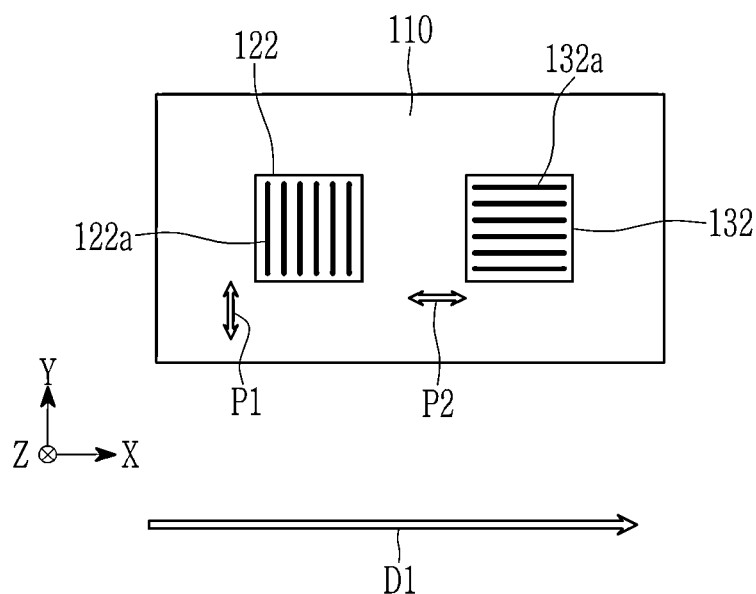

FIGS. 3A and 3B are schematic views illustrating polarization of a first polarizer and a second polarizer in the biosignal sensor of FIGS. 1 and 2.

Referring to FIGS. 3A and 3B, the first polarizer 122 and the second polarizer 132 may each include a plurality of patterns 122a and 132a extending in one direction. The plurality of patterns 122a of the first polarizer 122 may extend parallel to the first polarization direction P1, and the plurality of patterns 132a of the second polarizer 132 may extend in parallel with the second polarization direction P2. In other words, the plurality of patterns 122a of the first polarizer 122 may extend in the same direction as the first polarization direction P1, and the plurality of patterns 132a of the second polarizer 132 may extend in the same direction as the second polarization direction P2.

The plurality of patterns 122a and 132a of the first polarizer 122 and the second polarizer 132 may be, for example, a grid polarizer made of a metal, a dichroic dye, a polymer, or any combination thereof, but are not limited thereto. Each pattern 122a and 132a of the first polarizer 122 and the second polarizer 132 may have, for example, a width of about 10 nm to about 500 nm, and within the range, about 20 nm to about 400 nm, about 30 nm to about 300 nm, about 30 nm to about 200 nm, or about 30 nm to about 100 nm, but is limited thereto. The interval between adjacent patterns 122a and 132a may be, for example, about 10 nm to about 500 nm, and within the above range, about 20 nm to about 400 nm, about 30 nm to about 300 nm, about 30 nm to about 200 nm, or about 30 nm to about 100 nm, but is limited thereto.

The polarization direction (first polarization direction) P1 of the first polarizer 122 and the polarization direction (second polarization direction) P2 of the second polarizer 132 may be perpendicular or substantially perpendicular to each other. Herein, "substantially" includes an approximate range taking into account variations and errors within a normal range, for example, about ±5%, ±4%, ±3%, ±2%, or ±1%.

For example, one of the first polarization direction P1 of the first polarizer 122 or the second polarization direction P2 of the second polarizer 132 may be parallel or substantially parallel to the first direction D1 (e.g., X direction) that the first light-emitting element 121 and the first photo-detective element 131 are arranged, and the other of the first polarization direction P1 of the first polarizer 122 or the second polarization direction P2 of the second polarizer 132 may be perpendicular or substantially perpendicular to the first direction D1 (e.g., X direction).

For example, as shown in FIG. 3A, the first polarization direction P1 of the first polarizer 122 may be parallel or substantially parallel to the first direction D1 (e.g., X direction), and the second polarization direction P2 of the second polarizer 132 may be perpendicular or substantially perpendicular to the first direction D1 (e.g., X direction).

For example, as shown in FIG. 3B, the first polarization direction P1 of the first polarizer 122 may be perpendicular or substantially perpendicular to the first direction D1 (e.g., X direction), and the second polarization direction P2 of the second polarizer 132 may be parallel or substantially parallel to the first direction D1 (e.g., X direction).

Figure 4:
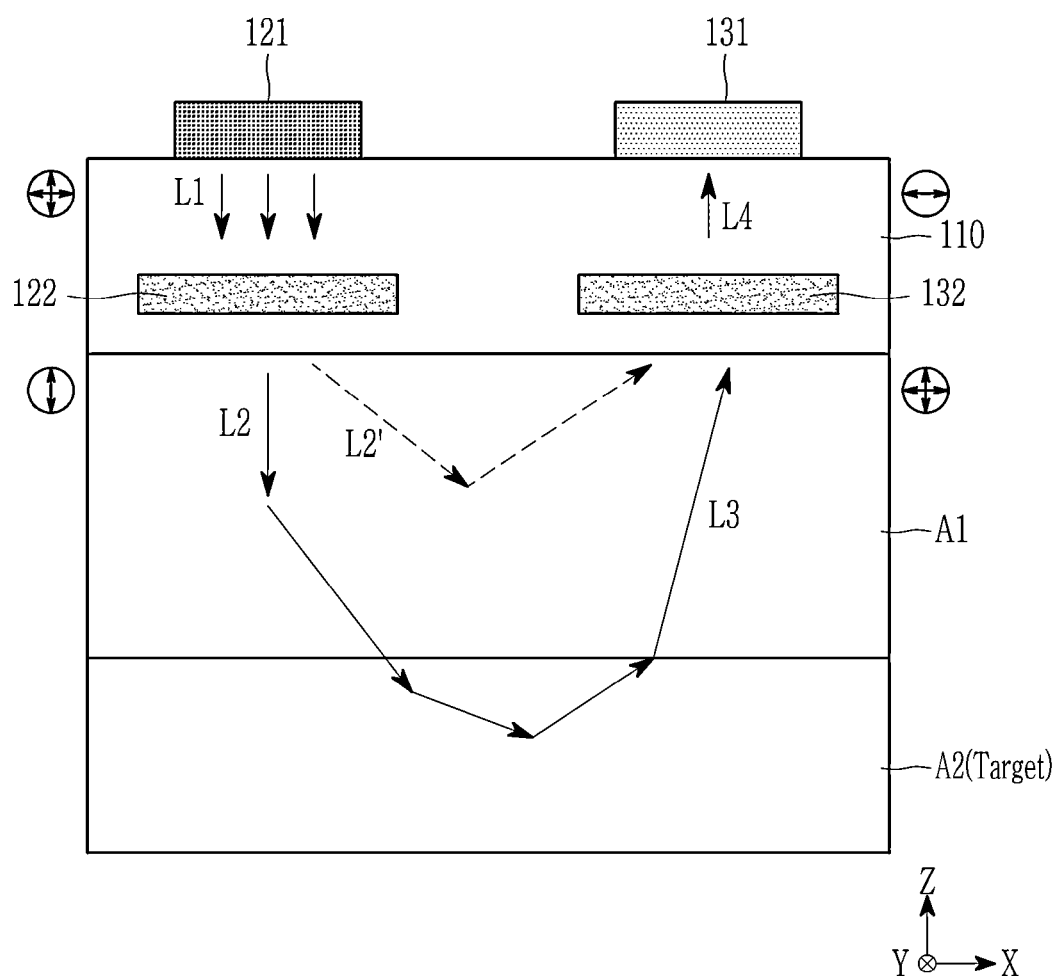
FIG. 4 is a schematic view showing an example of a path of light in the biosignal sensor of FIGS. 1 and 2.

FIG. 4 is a schematic view showing an example of a path of light in the biosignal sensor of FIGS. 1 and 2.

Referring to FIG. 4, the first light-emitting element 121 may be configured to emit unpolarized light L1, and when the unpolarized light L1 passes the first polarizer 122, only light including one polarization orthogonal component of two polarization orthogonal components, that is, a polarization component parallel to a first polarization direction P1 of the first polarizer 122 may be transmitted but light in a direction other than the first polarization direction P1 may be blocked and/or absorbed by the first polarizer 122. Therefore, the light passing through the first polarizer 122 from the first light-emitting element 121 may be light L2 that is linearly polarized in a direction parallel to the first polarization direction P1 of the first polarizer 122 (for example, in e.g., X direction or Y direction).

Most of the linearly polarized light L2 may pass through the skin tissue A1 to reach an in-vivo target A2 such as a blood vessel, and may be scattered and reflected. At this time, the scattered and reflected light L3 has lost a polarization property of the linearly polarized light L2 by scattering, and thus may be substantially unpolarized light having polarization components in all directions. Furthermore, since light scattered and reflected by the target A2 such as blood vessels located at a deep depth from the skin surface may be more scattered than light scattered by the skin tissue A1 located at a shallow depth from the skin surface, it may lose more polarization information polarized by the first polarizer 122 and thus the light L3 scattered and reflected by the in-vivo target A2 such as blood vessel may include more polarization components of a different direction from the first polarization direction of the first polarizer 122.

In this way, the scattered and reflected (unpolarized) light L3, while passing the second polarizer 132, may be converted into light L4 linearly polarized in a parallel direction (e.g., Y direction or X direction) to the second polarization direction P2 of the second polarizer 132 and introduced into the first photo-detective element 131. As described above, since the second polarization direction P2 of the second polarizer 132 is substantially perpendicular to the first polarization direction P1 of the first polarizer 122, the linearly polarized light L4 flowing in the first photo-detective element 131 may exclude the light of the parallel direction to the first polarization direction P1 of the first polarizer 122 (e.g., X direction or Y direction) but mainly include the light scattered and reflected by the in-vivo target A2 such as blood vessels. Accordingly, a signal to noise (STN) ratio of the scattered and reflected light may be increased.

On the other hand, a portion L2' of the linearly polarized light passing the first polarizer 122 may not reach the in-vivo target A2 such as blood vessels but be lost in the light-transmitting layer 110 or directly reflected toward the second polarizer 132 through the skin tissue A1. However, as described above, since the second polarization direction P2 of the second polarizer 132 is substantially perpendicular to the first polarization direction P1 of the first polarizer 122, the portion L2' of the linearly polarized light may not pass the second polarizer 132 but be blocked. Accordingly, the second polarizer 132 may be configured to effectively block the light not reaching the in-vivo target A2 such as blood vessels and thus having no biometric information and thus effectively reduce noises having no biometric information out of signals obtained from the first photo-detective element 131.

On the other hand, the polarization direction (first polarization direction) P1 of the first polarizer 122 and the polarization direction (second polarization direction) P2 of the second polarizer 132 with respect to the first direction D1 (e.g., X direction), in which the first light-emitting element 121 and the first photo-detective element 131 are arranged, may be ideally parallel or perpendicular as described above, but may have a particular (or, alternatively, predetermined) angle range with respect to the first direction D1 that the first light-emitting element 121 and the first photo-detective element 131 are arranged, as far as the noise reduction effect of the biosignal sensor 100 is secured, compared with when the first polarizer 122 and/or the second polarizer 132 are not included.

For example, the angle of the first polarization direction P1 or the second polarization direction P2 with respect to the first direction D1 that the first light-emitting element 121 and the first photo-detective element 131 are arranged (e.g., the first direction D1 in which the first light-emitting element 121 and the first photo-detective element 131 overlap) may be allowed within a range satisfying Relationship Equation 1.

$2S_1/S_0 < 1.0$       [Relationship Equation 1]

In Relationship Equation 1, $S_1$ is the amount of light measured by the first photo-detective element when the angle of the first polarization direction or the second polarization direction with respect to the first direction is $\theta$ degrees, and $S_0$ is an amount of light measured by the first photo-detective element when there is no second polarizer (e.g., when there are no polarizers between the first photo-detective element and the in-vivo target A2, etc., when light measured by the first photo-detective element does not pass through the second polarizer and is partially or completely non-polarized, when light measured by the first photo-detective element is not polarized in at least the second polarization direction P2, etc.).

Relationship Equation 1 may exhibit the noise reduction effect of the biosignal sensor 100 with the second polarizer 132, compared to when the second polarizer 132 is not included, and thus, it may exhibit a degree of noises due to the light L2' not reaching the in-vivo target A2 such as blood vessels. For example, when $2S_1/S_0$ is 1.0 with respect to the light L2' not reaching the in-vivo target A2 such as blood vessels, the biosignal sensor 100 has no noise reduction effect, but when $2S_1/S_0$ is less than 1.0, the biosignal sensor 100 has the noise reduction effect. The smaller $2S_1/S_0$, the larger the noise reduction effect due to the second polarizer 132. Herein, since maximum transmittance of the light passing the second polarizer 132 is about 50% out of the unpolarized light, $2S_1$ and $S_0$ are expressed as a ratio in order not to reflect a light loss due to the polarization of the second polarizer 132. For reference, the light L3 reflected by the in-vivo target A2 such as blood vessels may satisfy $2S_1/S_0 \approx 1.0$.

For example, when the second polarizer 132 is not included, the light L2' having no biometric information, which is described in FIG. 4, may all directly flow to the first photo-detective element 131 and act as very high noises. In consideration of this, when the angle of the first polarization direction P1 or the second polarization direction P2 with respect to the first direction D1 is within the range satisfying Relationship Equation 1, some noise reduction effects may be achieved.

For example, the angle $\theta$ of the first polarization direction P1 or the second polarization direction P2 with respect to the first direction D1 may be about −8.5 degrees to about +8.5 degrees (permissible range: about 17 degrees), and within the above range, about −6.5 degrees to about +6.5 degrees (permissible range: about 13 degrees), about −4.5 degrees to +4.5 degrees (permissible range: about 9 degrees), about −2.5 degrees to about +2.5 degrees (permissible range: about 5 degrees), or about −1.5 degrees to about +1.5 degrees (permissible range: about 3 degrees), and ideally 0 degrees (parallel).

For example, in FIG. 3A, an angle of the first polarization direction P1 with respect to the first direction D1 may be about −8.5 degrees to about +8.5 degrees (permissible range: about 17 degrees), and within the above range, about −6.5 degrees to about +6.5 degrees (permissible range: about 13 degrees), about −4.5 degrees to about +4.5 degrees (permissible range: about 9 degrees), about −2.5 degrees to about +2.5 degrees (permissible range: about 5 degrees), or about −1.5 degrees to about +1.5 degrees (permissible range: about 3 degrees), and ideally 0 degrees (parallel). As described above, the first polarization direction P1 and the second polarization direction P2 may be perpendicular or substantially perpendicular to each other.

For example, in FIG. 3B, an angle of the second polarization direction P2 with respect to the first direction D1 may be about −8.5 degrees to about +8.5 degrees (permissible range: about 17 degrees), and within the above range, about −6.5 degrees to about +6.5 degrees (permissible range: about 13 degrees), about −4.5 degrees to about +4.5 degrees (permissible range: about 9 degrees), about −2.5 degrees to about +2.5 degrees (permissible range: about 5 degrees), or about −1.5 degrees to about +1.5 degrees (permissible range: about 3 degrees), and ideally 0 degrees (parallel). As described above, the first polarization direction P1 and the second polarization direction P2 may be perpendicular or substantially perpendicular to each other.

When the biosignal sensor 100 is attached or placed close to the skin like a medical device-type sensor or a watch-type sensor, signal crosstalk may occur due to changes in the position and/or angle between the skin and the sensor due to skin motions. Herein, the changes in the position and/or angle between the skin and the sensor may occur due to the skin motions such as twisting, pulling, pressing, and/or the like. The signal crosstalk due to the changes in the position and/or angle between the skin and the sensor may deteriorate accuracy of the biometric information.

Specifically, as described above, a portion of the light incident toward the skin may be scattered and reflected in the skin tissue A1, and a portion of the light incident on the skin may be scattered and reflected in the in-vivo target A2 such as a blood vessel. The amount of light scattered and reflected in the skin tissue A1 may be generally constant over time, whereas the amount of light scattered and reflected in the in-vivo target A2 such as blood vessels may be periodically or aperiodically changed over time by biosignal changes such as a change of a blood flow due to vasoconstriction and vasorelaxation. The signals obtained from the scattered and reflected light may include a DC component scattered and reflected in the skin tissue and an AC component showing the biosignal changes such as a change of the blood flow, wherein when there are no skin motions, the constant DC component of the light scattered and reflected in the skin tissue and the AC component showing the biosignal changes may be clearly distinguished and have no crosstalk, but when there are skin motions such as twisting, pulling, and/or pressing, the position and angle of the first light-emitting element 121 and/or the first photo-detective element 131 may be changed, and accordingly, the DC component of the light scattered and reflected in the skin tissue may be largely changed and become unstable and thus be misunderstood with the AC component showing the biosignal changes such as a change of blood flow and work as noise and resultantly, deteriorate accuracy of the obtained biometric information.

In some example embodiments, as described above, only a particular (or, alternatively, predetermined) polarization component of the light emitted from the first light-emitting element 121 may enter the skin and then, polarization components that are substantially perpendicular to the particular (or, alternatively, predetermined) polarization component may be configured to selectively transmit the first photo-detective element 131, and thereby the unstable DC component due to skin scattering changes by the skin motions such as twisting, pulling, and/or pressing may be suppressed or prevented from flowing into the first photo-detective element 131 and thus the noise may be reduced. Accordingly, efficiency of the biosignal sensor 100 and the accuracy of the biometric information may be increased by reducing the noise due to the position and/or angle changes between the skin and the sensor and effectively increasing signals of the light scattered and reflected by the in-vivo target such as the blood vessels.

Hereinafter, another example of a biosignal sensor according to some example embodiments is described.

Figure 5:
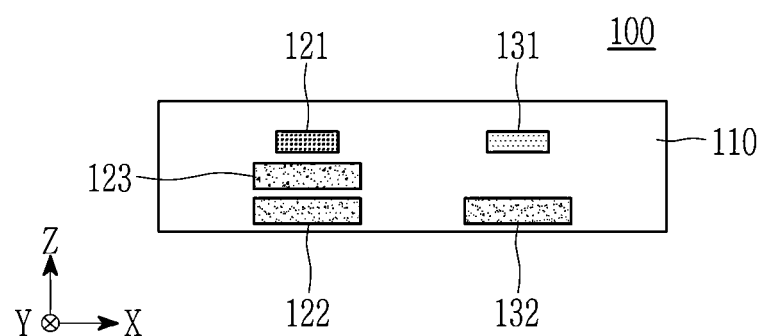
FIG. 5 is a cross-sectional view of another example of the biosignal sensor of FIG. 1 taken along line II-II'.
Figure 6:
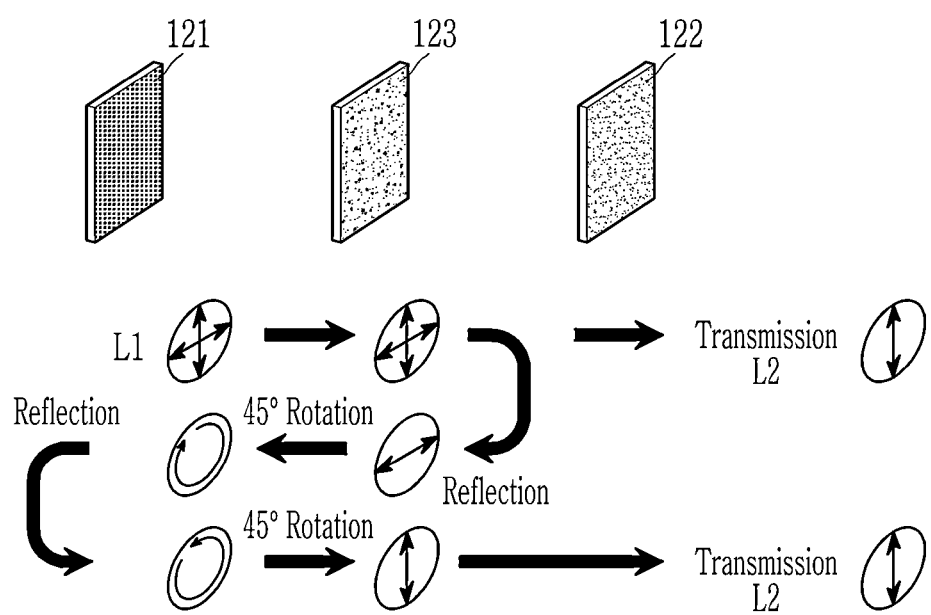
FIG. 6 is a schematic view showing a change in polarization of the biosignal sensor of FIG. 5.

FIG. 5 is a cross-sectional view of another example of the biosignal sensor of FIG. 1 taken along line II-II' and FIG. 6 is a schematic view showing a change in polarization of the biosignal sensor of FIG. 5.

Referring to FIG. 5, the biosignal sensor 100 according to some example embodiments includes a light-transmitting layer 110; a first light-emitting element 121; a first polarizer 122; a first photo-detective element 131; and a second polarizer 132, like some example embodiments, including the example embodiments shown in FIGS. 1-4. Herein, descriptions of the light-transmitting layer 110, the first light-emitting element 121, the first polarizer 122, the first photo-detective element 131, and the second polarizer 132 are the same as described above.

However, unlike some example embodiments, including the example embodiments shown in FIGS. 1-4, the biosignal sensor 100 according to some example embodiments further includes a phase retarder 123. The phase retarder 123 may be disposed at a position through which light emitted from the first light-emitting element 121 passes, and may be disposed in the light-transmitting layer 110, for example, between the first light-emitting element 121 and the first polarizer 122 (e.g., between the first light-emitting element 121 and the first polarizer 122 in the Z-direction, or vertical direction). The phase retarder 123 may be, for example, a λ/4 phase retarder.

Referring to FIG. 6, the phase retarder 123 may change a polarization direction of reflected light without passing the first polarizer 122 (e.g., left-handed circularly polarized light) and change again a polarization direction of the light reflected by the first light-emitting element 121 and thus convert it into the linearly polarized light L2 in a parallel direction to the first polarization direction P1 of the first polarizer 122, so that the linearly polarized light L2 may transmit the first polarizer 122. Accordingly, light conversion efficiency may be improved by increasing a dose of the linearly polarized light L2 passing the first polarizer 122 out of the light L1 emitted from the first light-emitting element 121. For example, a ratio of the linearly polarized light L2 to the light L1 emitted from the first light-emitting element 121 may be, for example, greater than or equal to about 60%, greater than or equal to about 65%, greater than or equal to about 70%, or greater than or equal to about 75%.

Hereinafter, another example of a biosignal sensor according to some example embodiments is described.

Figure 7:
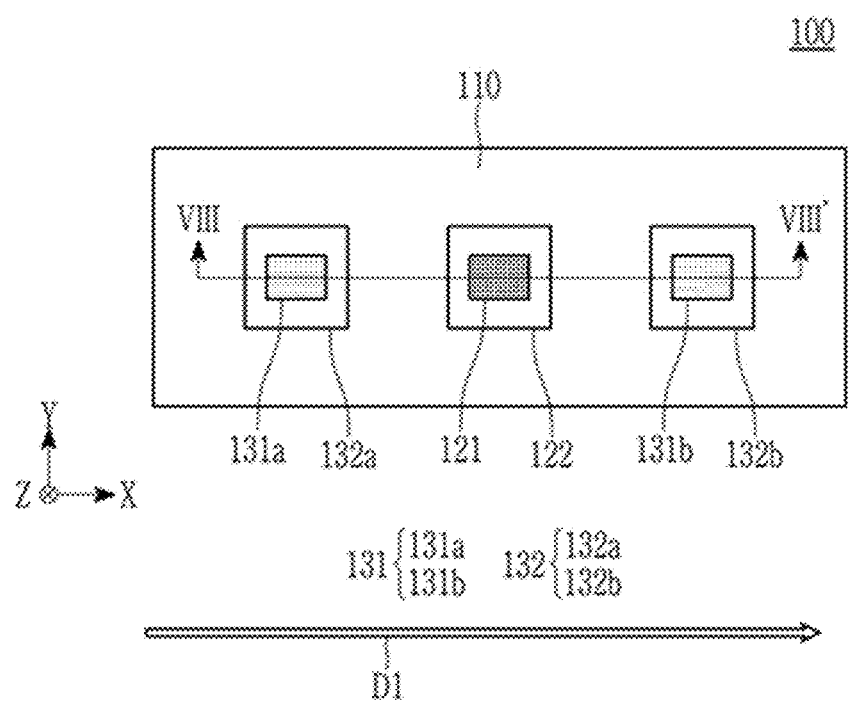
FIG. 7 is a plan view showing another example of a biosignal sensor according to some example embodiments.
Figure 8:
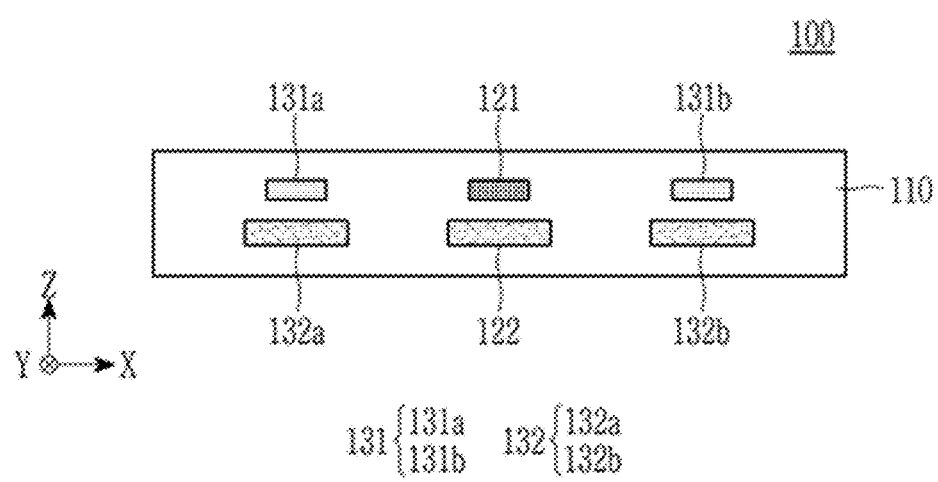
FIG. 8 is a cross-sectional view of the biosignal sensor of FIG. 7 taken along line VIII-VIII'.

FIG. 7 is a plan view showing another example of a biosignal sensor according to some example embodiments, and FIG. 8 is a cross-sectional view of the biosignal sensor of FIG. 7 taken along line VIII-VIII'.

Referring to FIGS. 7 and 8, another example of the biosignal sensor 100 according to some example embodiments includes a light-transmitting layer 110, a first light-emitting element 121, a first polarizer 122, a first photo-detective element 131, and a second polarizer 132, like some example embodiments, including the example embodiments shown in FIGS. 1-4. In addition, although not shown, a phase retarder 123 illustrated in FIG. 5 may be optionally further included between the first light-emitting element 121 and the first polarizer 122. Detailed descriptions of the light-transmitting layer 110, the first light-emitting element 121, the first polarizer 122, the first photo-detective element 131, and the second polarizer 132 are the same as described above.

However, another example of the biosignal sensor 100 according to some example embodiments includes a plurality of first photo-detective elements 131*a* and 131*b* at both sides (e.g., opposite sides) of the first light-emitting element 121 along the first direction D1, unlike some example embodiments, including the example embodiments shown in FIGS. 1-4. The first photo-detective elements 131*a* and 131*b* at both sides (e.g., opposite sides) of the first light-emitting element 121 are disposed inside or above the light-transmitting layer 110 at a particular (or, alternatively, predetermined) interval and may be parallel to each other along the first direction D1 (e.g., X direction). The second polarizers 132*a* and 132*b* are disposed under each first photo-detective element 131*a* and 131*b*, and the second polarizers 132*a* and 132*b* may be respectively overlapped with the first photo-detective elements 131*a* and 131*b* along the thickness direction (e.g., Z direction) of the light-transmitting layer 110. The first light-emitting element 121 may be a common light source of the plurality of first photo-detective elements 131*a* and 131*b*.

As described above, the polarization direction (first polarization direction) P1 of the first polarizer 122 and the polarization direction (second polarization direction) P2 of the second polarizers 132*a* and 132*b* may be perpendicular or substantially perpendicular. In addition, since the first photo-detective elements 131*a* and 131*b* are disposed parallel along the first direction D1 (e.g., X direction) of the first light-emitting element 121, one of the first polarization direction P1 of the first polarizer 122 or the second polarization direction P2 of the second polarizers 132*a* and 132*b* may be parallel or substantially parallel to the first direction D1 (e.g., X direction) that the first light-emitting element 121 and the first photo-detective element 131 are arranged, while the other of the first polarization direction P1 of the first polarizer 122 or the second polarization direction P2 of the second polarizers 132 and 132*b* may be perpendicular or substantially perpendicular to the first direction D1 (e.g., X direction).

Hereinafter, another example of a biosignal sensor according to some example embodiments is described.

Figure 9:
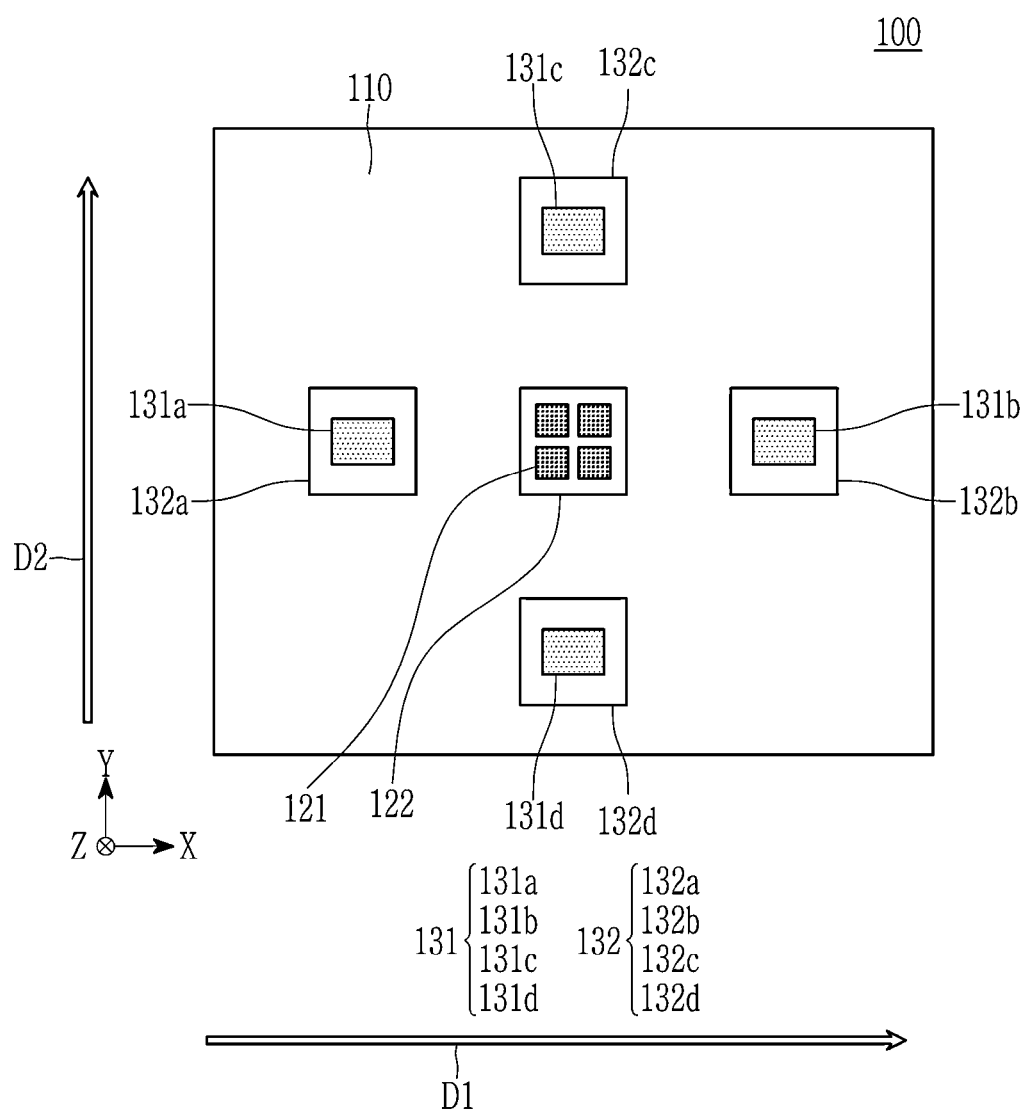
FIG. 9 is a plan view showing another example of a biosignal sensor according to some example embodiments.

FIG. 9 is a plan view showing another example of a biosignal sensor according to some example embodiments.

Referring to FIG. 9, another example of the biosignal sensor 100 according to some example embodiments includes a light-transmitting layer 110, a first light-emitting element 121, a first polarizer 122, and a first photo-detective element 131, and a second polarizer 132, like some example embodiments, including the example embodiments shown in FIGS. 1-4. In addition, although not shown, a phase retarder 123 illustrated in FIG. 5 may be optionally further included between the first light-emitting element 121 and the first polarizer 122. Detailed descriptions of the light-transmitting layer 110, the first light-emitting element 121, the first polarizer 122, the first photo-detective element 131, and the second polarizer 132 are the same as described above.

However, another example of the biosignal sensor 100 according to some example embodiments, unlike some example embodiments, including the example embodiments shown in FIGS. 1-4, includes a plurality of first photo-detective elements 131*a* and 131*b* at both sides (e.g., opposite sides) of the first light-emitting element 121 along the first direction D1 (e.g., X direction) and a plurality of first photo-detective elements 131*c* and 131*d* at both sides (e.g., opposite sides) of the first light-emitting element 121 along the second direction D2 (e.g., Y direction) which is perpendicular to the first direction D1. For example, at least some first photo-detective elements (e.g., 131*a*, 131*b*) of the plurality of first photo-detective elements 131*a*, 131*b*, 131*c*, 131*d* may be at opposite sides of the first light-emitting element 121 along the first direction D1 such that the first light-emitting element 121 is between the at least some first photo-detective elements (e.g., 131*a*, 131*b*) in the first direction D1. Additionally, some other first photo-detective elements (e.g., 131*c*, 131*d*) of the plurality of first photo-detective elements 131*a*, 131*b*, 131*c*, 131*d* may be at opposite sides of the first light-emitting element 121 along a second direction D2 that is perpendicular to the first direction D1, such that the first light-emitting element 121 is between the some other first photo-detective elements (e.g., 131*c*, 131*d*) in the second direction D2 that is perpendicular to both the first direction D1 and the Z-direction (e.g., vertical direction). In other words, the first photo-detective elements 131*a*, 131*b*, 131*c*, and 131*d* are respectively disposed at the left, right, upper, and lower sides with the first light-emitting element 121 as a center. The first photo-detective elements 131*a*, 131*b*, 131*c*, and 131*d* are respectively disposed at a particular (or, alternatively, predetermined) interval from the first light-emitting element 121, wherein the intervals from the first light-emitting element 121, for example, may be substantially the same. On the other hand, the first light-emitting element 121 may be included in plural for sufficient light emission, and the plurality of first light-emitting elements 121 may be configured to emit light in the same or different wavelength regions.

The second polarizers 132*a*, 132*b*, 132*c*, and 132*d* may be disposed under each of the first photo-detective elements 131*a*, 131*b*, 131*c*, and 131*d*, and the second polarizers 132*a*, 132*b*, 132*c*, and 132*d* may be overlapped with the first photo-detective elements 131*a*, 131*b*, 131*c*, and 131*d* along the thickness direction (e.g., Z direction) of the light-transmitting layer 110.

As described above, the polarization direction (first polarization direction) P1 of the first polarizer 122 and the polarization direction (second polarization direction) P2 of the second polarizers 132*a*, 132*b*, 132*c*, and 132*d* may be perpendicular or substantially perpendicular. In addition, since the first photo-detective elements 131*a*, 131*b*, 131*c*, and 131*d* are disposed parallel to the first light-emitting element 121 along the first direction D1 (e.g., X direction) or the second direction D2 (e.g., Y direction), one of the first polarization direction P1 of the first polarizer 122 or the second polarization direction P2 of the second polarizers 132*a*, 132*b*, 132*c*, and 132*d* may be parallel or substantially parallel to the first direction D1 (e.g., X direction) that the first light-emitting element 121 and the first photo-detective elements 131*a*, 131*b*, 131*c*, and 131*d* are arranged or the second direction D2 (e.g., Y direction), while the other of the first polarization direction P1 of the first polarizer 122 or the second polarization direction P2 of the second polarizers 132*a*, 132*b*, 132*c*, and 132*d* may be perpendicular or substantially perpendicular to the first direction D1 (e.g., X direction) or the second direction D2 (e.g., Y direction).

Hereinafter, another example of a biosignal sensor according to some example embodiments is described.

Figure 10:
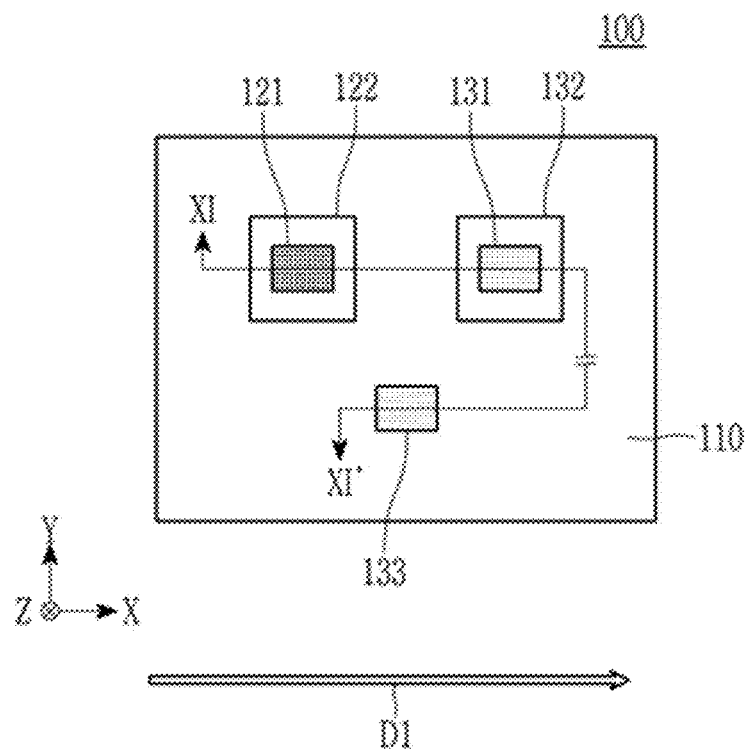
FIG. 10 is a plan view showing another example of a biosignal sensor according to some example embodiments.
Figure 11:
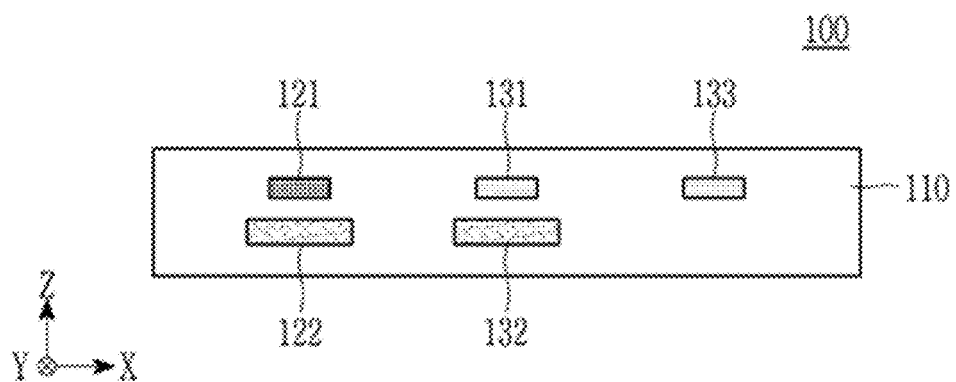
FIG. 11 is a cross-sectional view of the biosignal sensor of FIG. 10 taken along line XI-XI'.

FIG. 10 is a plan view showing another example of a biosignal sensor according to some example embodiments, and FIG. 11 is a cross-sectional view of the biosignal sensor of FIG. 10 taken along line XI-XI'.

Referring to FIGS. 10 and 11, another example of the biosignal sensor 100 according to some example embodiments includes a light-transmitting layer 110, a first light-emitting element 121, a first polarizer 122, a first photo-detective element 131, and a second polarizer 132, like some example embodiments, including the example embodiments shown in FIGS. 1-4. In addition, although not shown, a phase retarder 123 illustrated in FIG. 5 may be optionally further included between the first light-emitting element 121 and the first polarizer 122. Detailed descriptions of the light-transmitting layer 110, the first light-emitting element 121, the first polarizer 122, the first photo-detective element 131, and the second polarizer 132 are the same as described above.

However, another example of the biosignal sensor 100 according to some example embodiments further includes a second photo-detective element 133, unlike some example embodiments, including the example embodiments shown in FIGS. 1-4. Unlike the first photo-detective element 131, the second photo-detective element 133 is not overlapped with the second polarizer 132 (e.g., not overlapped with the second polarizer 132 and/or exposed from the second polarizer 132 in the thickness direction of the light-transmitting layer 110, the Z-direction, and/or the vertical direction). That is, the second polarizer 132 is disposed only under the first photo-detective element 131 and not under the second photo-detective element 133. Accordingly, light linearly polarized by the second polarizer 132 may be introduced into the first photo-detective element 131 as described above, whereas light that is not separately linearly polarized may be introduced into the second photo-detective element 133.

The second photo-detective element 133 may be the same as the first photo-detective element 131 except that it is not overlapped with the second polarizer 132. In other words, the second photo-detective element 133 may include, for example, an inorganic photodiode or an organic photoelectric conversion element, and may include, for example, a photoelectric conversion layer including an inorganic semiconductor, an organic semiconductor, and/or an organic-inorganic semiconductor between a pair of electrodes and an electrode and includes. The light emitted from the first light-emitting element 121 passes through the light-transmitting layer 110 and is scattered and reflected in an in-vivo target such as a blood vessel, and the scattered and reflected light passes through the light-transmitting layer 110 again and is absorbed and photoelectrically converted in the second photo-detective element 133 to obtain a biosignal.

The first light-emitting element 121 and the second photo-detective element 133 may be disposed parallel along a third direction (e.g., a direction inclined at a particular (or, alternatively, predetermined) angle with respect to D1 and D2, respectively) which is different from the first direction D1 (e.g., X direction) that the first light-emitting element 121 and the first photo-detective element 131 are arranged or the second direction D2 (e.g., Y direction) perpendicular to the first direction D1. The third direction may not be parallel or perpendicular to the first direction or the second direction, for example, inclined at about 10° to about 80°, about 20° to about 70°, about 30° to about 60°, about 40° to about 50°, or about 45° with respect to the first direction D1 or the second direction D2. In other words, the first photo-detective element 131 and the second photo-detective element 133 are not horizontally or vertically disposed. The third direction may be perpendicular to the Z-direction (e.g., vertical direction).

The first photo-detective element 131 and the second photo-detective element 133 may be selectively operated depending on whether or not the attachment or wearing portion of a user moves, for example, in no movement state (stop state), the second photo-detective element 133 may be selectively operated, but in a motion state (movement state), the first photo-detective element 131 may be selectively operated.

As described above, when the first polarizer 122 and the second polarizer 132 are respectively disposed under the first light-emitting element 121 and the first photo-detective element 131, since a particular (or, alternatively, predetermined) polarization component alone out of the light emitted from the first light-emitting element 121 is selectively made to enter the skin, and the first photo-detective element 131 may be selectively transmit a polarization component substantially perpendicular to the particular (or, alternatively, predetermined) polarization component, unstable DC components due to skin scattering changes caused by skin motions such as twisting, pulling, and/or pressing may be suppressed or prevented from flowing in the first photo-detective element 131, reducing noises. Accordingly, efficiency of the biosignal sensor 100 and the accuracy of the biometric information may be increased by reducing the noise due to the position and/or angle changes between the skin and the biosignal sensor 100 and effectively increasing signals of the light scattered and reflected in the in-vivo target such as the blood vessels.

On the contrary, the second polarizer 132 may be configured to theoretically transmit about 50% of incident light at maximum and thus have a large light loss. For example, the second polarizer 132 may be configured to transmit about 50% or less of light flowing in the first photo-detective element 131 and thus have low light efficiency. In addition, when there are no aforementioned skin motions such as twisting, pulling, and/or pressing, the noise reduction effect may be small or unnecessary.

Accordingly, the aforementioned noise reduction effect and the light efficiency improvement effect may be simultaneously achieved by selectively operating the first photo-detective element 131 with a polarizer and the second photo-detective element 133 without the polarizer depending on whether or not the attachment or wearing portion of a user moves. For example, when the biosignal sensor 100 is attached to the skin or placed close to the skin like a medical device-type sensor or a watch-type sensor, the biosignal sensor 100 may realize the noise reduction effect by selectively operating the first photo-detective element 131 when the skin motions such as twisting, pulling, and/or pressing are detected and also, high light efficiency without a light loss by selectively operating the second photo-detective element 133 in no motion state (in the stop state).

Another example of a biosignal sensor according to some example embodiments is described.

Figure 12:
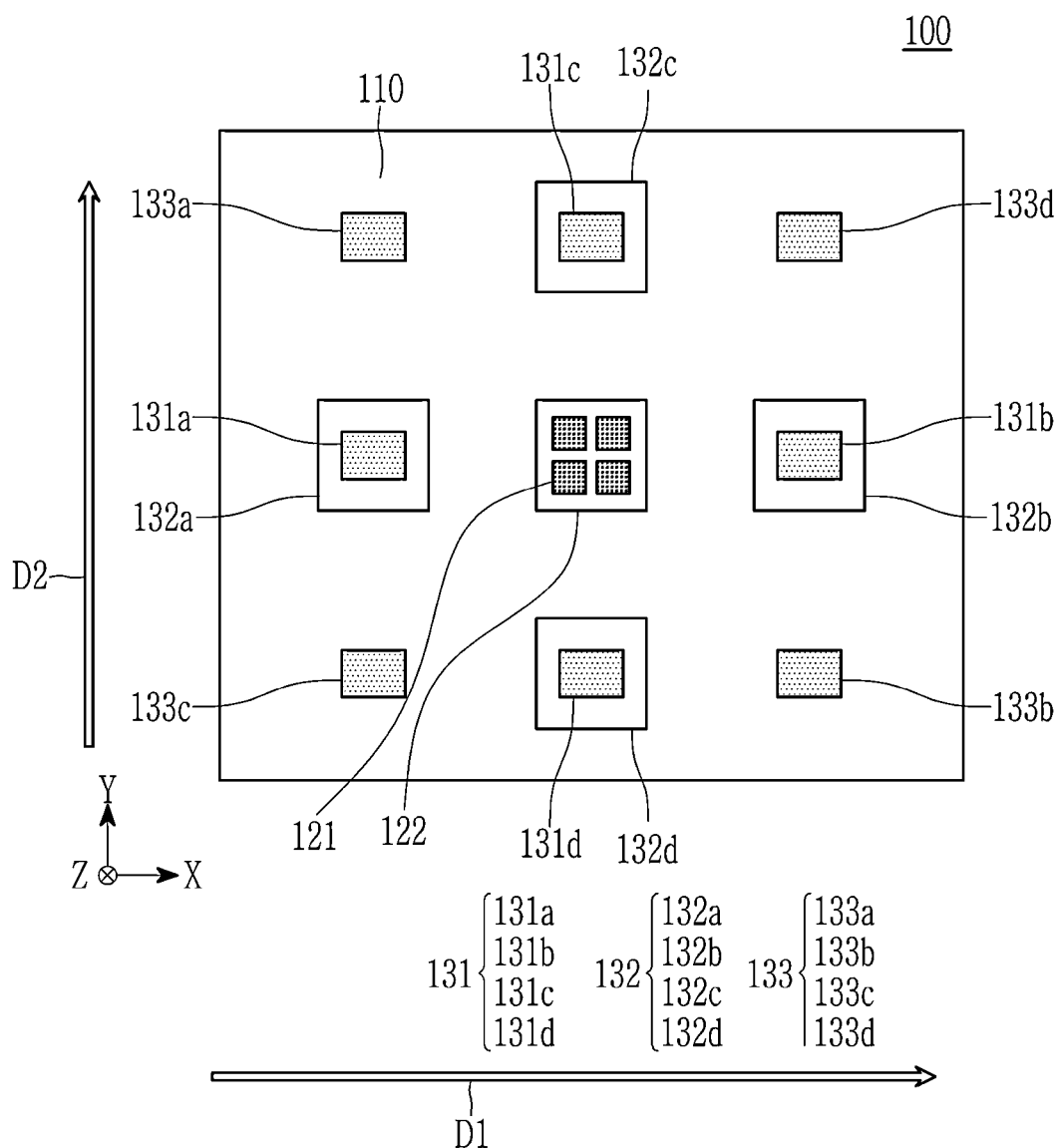
FIG. 12 is a plan view showing another example of a biosignal sensor according to some example embodiments.

FIG. 12 is a plan view showing another example of a biosignal sensor according to some example embodiments.

Referring to FIG. 12, another example of the biosignal sensor 100 according to some example embodiments includes a light-transmitting layer 110, a first light-emitting element 121, a first polarizer 122, a first photo-detective element 131, a second polarizer 132, and a second photo-detective element 133, like some example embodiments, including the example embodiments shown in FIGS. 1-4. In addition, although not shown, a phase retarder 123 illustrated in FIG. 5 may be optionally further included between the first light-emitting element 121 and the first polarizer 122. The light-transmitting layer 110, the first light-emitting element 121, the first polarizer 122, the first photo-detective element 131, the second polarizer 132, and the second photo-detective element 133 are the same as described above.

However, another example of the biosignal sensor 100 according to some example embodiments, unlike some example embodiments, including the example embodiments shown in FIGS. 1-4, includes the plurality of first photo-detective elements 131a and 131b at both sides (e.g., opposite sides) of the first light-emitting element 121 along the first direction D1, the plurality of first photo-detective elements 131c and 131d at both sides (e.g., opposite sides) of the first light-emitting element 121 along the second direction D2 perpendicular to the first direction D1, the plurality of second photo-detective elements 133a and 133b at both sides (e.g., opposite sides) of the first light-emitting element 121 along the third direction respectively different from the first direction D1 and the second direction D2, and a plurality of second photo-detective elements 133c and 133d at both sides (e.g., opposite sides) of the first light-emitting element 121 along a fourth direction respectively different from the first direction D1, the second direction D2, and the third direction. For example, the third direction and the fourth direction may be independently inclined at about 10° to about 80°, about 20° to about 70°, about 30° to about 60°, about 40° to about 50°, or about 45° with respect to the first direction D1 or the second direction D2, for example, the third direction and the fourth direction may be perpendicular each other. In other words, each first photo-detective element 131a, 131b, 131c, and 131d may be disposed at the left, right, upper, and lower side with the first light-emitting element 121 as the center, and each second photo-detective element 133a, 133b, 133c, and 133d may be respectively disposed at a diagonal position with the first light-emitting element 121 as the center. The first light-emitting element 121 may be a common light source of the plurality of first photo-detective elements 131a, 131b, 131c, and 131d and the plurality of second photo-detective elements 133a, 133b, 133c, and 133d and may be included in plural for sufficient light emission.

Referring to FIG. 12, in some example embodiments, some first photo-detective elements (e.g., 131a, 131b) of plurality of first photo-detective elements 131a, 131b, 131c, 131d may be at one or opposite sides of the first light-emitting element along 121 the first direction D1, some other first photo-detective elements (e.g., 131c, 131d) of the plurality of first photo-detective elements 131a, 131b, 131c, 131d may be at one or opposite sides of the first light-emitting element 121 along a second direction D2 that is perpendicular to the first direction D2 and a vertical direction (e.g., Z-direction), some second photo-detective elements (e.g., 133a, 133b) of the plurality of second photo-detective elements 133a, 133b, 133c, 133d may be at one or opposite sides of the first light-emitting element 121 along a third direction, the third direction being different from the first direction D1 and the second direction D2 (e.g., at 45 degrees to each of the first and second directions D1 and D2) and perpendicular to the vertical direction (e.g., Z-direction), and some other second photo-detective elements (e.g., 133c, 133d) of the plurality of second photo-detective elements 133a, 133b, 133c, 133d may be at one or opposite sides of the first light-emitting element 121 along a fourth direction, the fourth direction being different from the first direction D2, the second direction D2, and the third direction (e.g., at 45 degrees to each of the first and second directions D1 and D2 and perpendicular to the third direction) and perpendicular to the vertical direction (e.g., Z-direction).

As described above, the first photo-detective elements 131a, 131b, 131c, and 131d and the second photo-detective elements 133a, 133b, 133c, and 133d may be selectively operated depending on whether or not the attachment or wearing portion of a user moves, for example, in no movement state (stop state), the second photo-detective elements 133a, 133b, 133c, and 133d may be selectively operated, but in the motion state, the first photo-detective elements 131a, 131b, 131c, and 131d may be selectively operated, simultaneously realizing the noise reduction effect and the light efficiency improvement effect. Detailed description is as described above.

Hereinafter, another example of a biosignal sensor according to some example embodiments is described.

Figure 13:
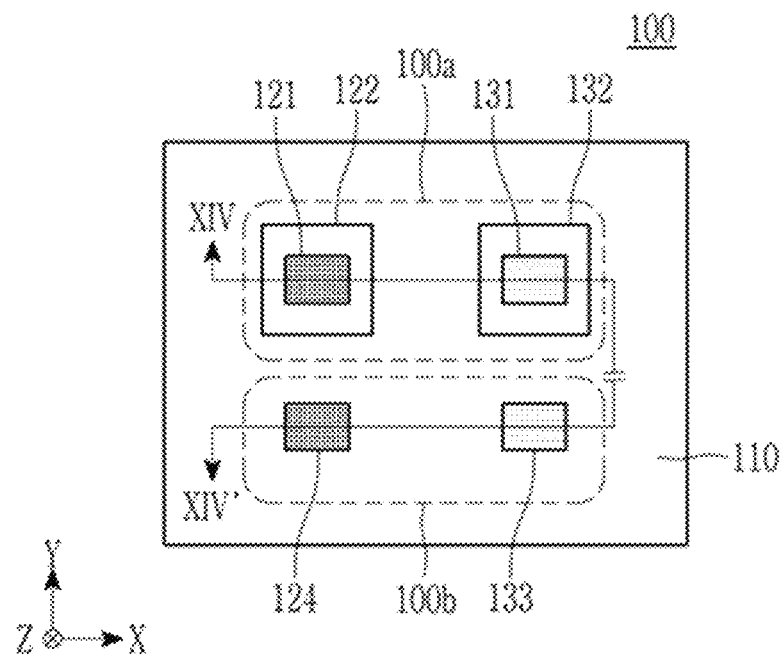
FIG. 13 is a plan view showing another example of a biosignal sensor according to some example embodiments.
Figure 14:
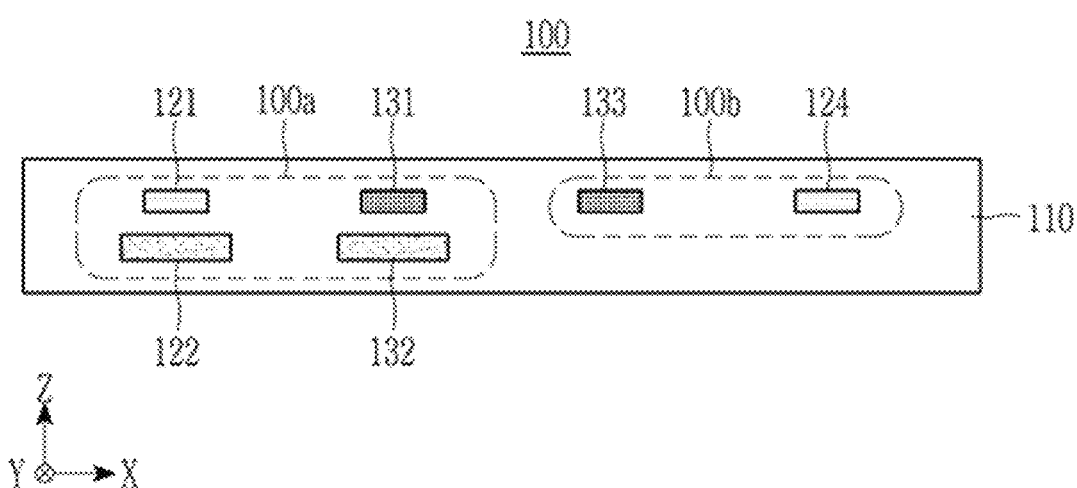
FIG. 14 is a cross-sectional view of the biosignal sensor of FIG. 13 taken along line XIV-XIV'.

FIG. 13 is a plan view showing another example of a biosignal sensor according to some example embodiments, and FIG. 14 is a cross-sectional view of the biosignal sensor of FIG. 13 taken along line XIV-XIV'.

Referring to FIGS. 13 and 14, another example of the biosignal sensor 100 according to some example embodiments includes a light-transmitting layer 110, a first light-emitting element 121, a first polarizer 122, a first photo-detective element 131, a second polarizer 132, and a second photo-detective element 133, like some example embodiments, including the example embodiments shown in FIGS. 1-4. The light-transmitting layer 110, the first light-emitting element 121, the first polarizer 122, the second polarizer 132, the first photo-detective element 131, and the second photo-detective element 133 are the same as described above.

However, another example of the biosignal sensor 100 according to some example embodiments further includes a second light-emitting element 124 in addition to the second photo-detective element 133, unlike some example embodiments, including the example embodiments shown in FIGS. 1-4. Unlike the first light-emitting element 121, the second light-emitting element 124 is not overlapped with the first polarizer 122 (e.g., is not overlapped with the first polarizer 122 and/or is exposed from the first polarizer 122 in the thickness direction of the light-transmitting layer 110, the Z-direction, and/or the vertical direction). That is, the first polarizer 122 is disposed only under the first light-emitting element 121 and not under the second light-emitting element 124. Accordingly, the second light-emitting element 124 may be configured to emit unpolarized light.

The second light-emitting element 124 may be the same as the first light-emitting element 121 except that it is not overlapped with the first polarizer 122. That is, the second light-emitting element 124 may include, for example, an inorganic light-emitting diode, an organic light-emitting diode, an organic-inorganic light-emitting diode, or a micro light-emitting diode and may include, for example, a light emitting layer including a light-emitting body such as organic light-emitting materials, inorganic light-emitting materials, quantum dots, and/or perovskite.

The first biosignal sensor 100a may further include a phase retarder 123 (e.g., between the first light-emitting element 121 and the first polarizer 122). The biosignal sensor 100 of FIGS. 13-14 may be a skin-attachable photoplethysmography (PPG) sensor.

The first light-emitting element 121 and the first photo-detective element 131 may form a pair to provide the first biosignal sensor 100a, and the second light-emitting element 124 and the second photo-detective element 133 may form a pair to provide the second biosignal sensor 100b. The first biosignal sensor 100a and the second biosignal sensor 100b may operate independently. That is, when the first biosignal sensor 100a is operated, the light emitted from the first light-emitting element 121 passes through the light-transmitting layer 110 and is scattered and reflected in an in-vivo target such as a blood vessel, and the scattered and reflected light passes through the light-transmitting layer 110 again and is absorbed and photoelectrically converted in the first photo-detective element 131 to obtain a biosignal. In addition, when the second biosignal sensor 100b is operated, the light emitted from the second light-emitting element 124 passes through the light-transmitting layer 110 and is scattered and reflected in an in-vivo target such as a blood vessel, and the scattered and reflected light passes through the light-transmitting layer 110 again and is absorbed and photoelectrically converted in the second photo-detective element 133 to obtain a biosignal.

The first biosignal sensor 100a and the second biosignal sensor 100b may be selectively operated depending on whether or not the attachment or wearing portion of a user moves, for example, in no movement state (stop state), the second biosignal sensor 100b may be selectively operated, but in the motion state, the first biosignal sensor 100a may be selectively operated.

As described above, the first biosignal sensor 100a including the first light-emitting element 121 provided with the first polarizer 122 and the first photo-detective element 131 provided with the second polarizer 132 may reduce noise due to changes in the position and/or angle between the skin and the biosignal sensor 100 by selectively transmitting light, and may effectively increase the signal of light scattered and reflected in an in-vivo target such as blood vessels, and thereby may increase efficiency and increase the accuracy of biometric information.

On the contrary, the first polarizer 122 and the second polarizer 132 may be configured to theoretically transmit about 50% of incident light at maximum and thus have a large light loss. For example, the first polarizer 122 may be configured to transmit about 50% or less of light emitted from the first light-emitting element 121, and the second polarizer 132 may be configured to transmit about 50% or less of light flowing in the first photo-detective element 131, and thus have low light efficiency. In addition, when there are no aforementioned skin motions such as twisting, pulling, and/or pressing, the aforementioned noise reduction effect may be small or unnecessary.

Accordingly, the aforementioned noise reduction effect and the light efficiency improvement effect may be simultaneously realized by selectively operating the first biosignal sensor 100a and the second biosignal sensor 100b depending on whether or not the attachment or wearing portion of a user moves. For example, when the biosignal sensor 100 is attached or placed close to the skin like a medical device-type sensor or a watch-type sensor, when the skin motions such as twisting, pulling, and/or pressing are detected, the noise reduction effect may be obtained by selectively operating the first biosignal sensor 100a, but when there are no skin motions (in the stop state), the high light efficiency of the biosignal sensor 100 may be realized without the light loss by operating the second biosignal sensor 100b. As shown in FIGS. 13-14, the biosignal sensor 100 may include a first biosignal sensor 100a including a first photo-detective element 131 and a second polarizer 132 that is overlapped with the first photo-detective element 131 in a vertical direction (e.g., Z-direction) and a second biosignal sensor 100b that includes a second photo-detective element 133 that does not overlap with any polarizers in the vertical direction (e.g., Z-direction), where the first biosignal sensor 100a and the second biosignal sensor 100b are configured to operate independently. As shown, the second biosignal sensor 100b may not include any polarizers. As shown, the first light-emitting element 121 may be overlapped with a separate polarizer (e.g., first polarizer 122) in the vertical direction (e.g., Z-direction).

In some example embodiments, referring to FIGS. 12-14, the biosignal sensor 100 may include a plurality of first biosignal sensors 100a, wherein some first biosignal sensors 100a of the plurality of first biosignal sensors 100a are at one or opposite sides of the first light-emitting element 121 along a first direction D1 that is perpendicular to the vertical direction (e.g., Z-direction), and some other first biosignal sensors 100a of the plurality of first biosignal sensors 100a are at one or opposite sides of the first light-emitting element 121 along a second direction D2 that is perpendicular to both the first direction D1 and the vertical direction.

In some example embodiments, referring to FIGS. 12-14, the biosignal sensor 100 may further include a plurality of second biosignal sensors 100b, where some second biosignal sensors 100b of the plurality of the second biosignal sensors 100b are at one or opposite sides of the first light-emitting element 121 along a third direction that is different from both the first direction D1 and the second direction D2 and perpendicular to the vertical direction (e.g., Z-direction), and some other second biosignal sensors 100b of the plurality of the second biosignal sensors 100b are at one or opposite sides of the first light-emitting element 121 along a fourth direction that is different from the first direction, the second direction, and the third direction and perpendicular to the vertical direction.

Figure 15:
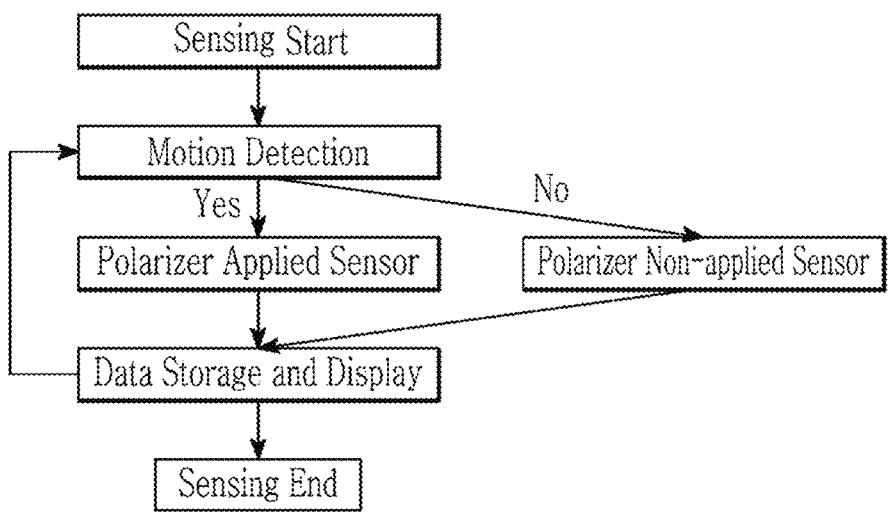
FIG. 15 is a view illustrating an example of a method of operating a biosignal sensor according to some example embodiments.
Figure 16:
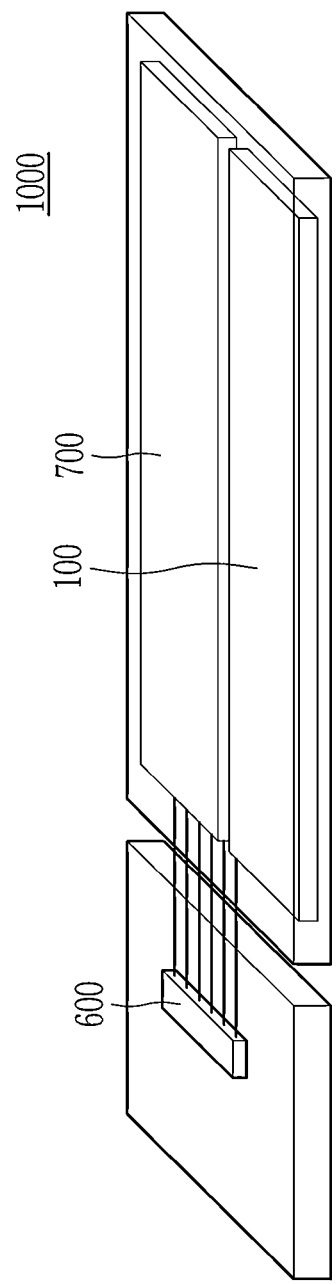
FIG. 16 is a schematic view showing an example of a sensor system according to some example embodiments.

FIG. 15 is a view illustrating an example of a method of operating a biosignal sensor according to some example embodiments. The method may be performed to operate any biosignal sensor 100 according to any of the example embodiments. The method may be performed by any processing circuitry according to any of the example embodiments, including for example the IC and/or processor 600 of the sensor system 1000 as shown in FIG. 16.

Referring to FIG. 15, a method of operating the biosignal sensor 100 according to some example embodiments may include detecting the motion of an attachment or wearing portion of a user, such as a user's human body, selectively driving the first biosignal sensor 100a or the second biosignal sensor 100b depending on (e.g., according to) the detected motion, and obtaining a biosignal from the first biosignal sensor 100a or the second biosignal sensor 100b. For example, the selectively driving of the first biosignal sensor 100a or the second biosignal sensor 100b may include selectively driving the first biosignal sensor 100a when the motion of the attachment or wearing portion is detected (e.g., in response to the motion of the attachment or wearing portion being detected) and selectively driving the second biosignal sensor 100b when the motion of the attachment or wearing portion is not detected (e.g., in response to the motion of the attachment or wearing portion not being detected). Herein, the attachment or wearing portion may be, for example, a wrist, an ankle, an arm, a neck, and/or a chest of a user, but is not limited thereto. The biosignal may be, for example, a PPG signal.

The aforementioned biosignal sensor 100 may be applied in the form of an array arranged along rows and/or columns. It is possible to more easily and accurately detect the biosignal by applying the biosignal sensor 100 in the form of an array.

The aforementioned biosignal sensor 100 may be applied to various sensor systems to collect biosignal information, and may be used to obtain biosignals temporarily or in real time. The biosignal sensor 100 may be applied to, for example, a wearable bioelectronic device or a skin attachable device that is directly attached to the skin, and may be used to obtain a physiological signal such as blood flow temporarily or in real time, but is not limited thereto. The sensor system may be, for example, a patch-type biosignal sensor system, a band-type biosignal sensor system, or a watch-type biosignal sensor system.

FIG. 16 is a schematic view showing an example of a sensor system according to some example embodiments.

Referring to FIG. 16, the sensor system 1000 according to some example embodiments may be, for example, a wearable biosignal sensor system in the form of a patch, a band, or a watch. The aforementioned biosignal sensor 100; an IC and/or processor 600 for processing a biosignal obtained from the biosignal sensor 100 and a display region 700 displaying the obtained biosignal as various characters and/or images may be included. The sensor system 1000 may further include a motion sensor (e.g., motion detecting sensor) configured to detect the motion of the aforementioned wearing or attachment portion.

As shown, the IC and/or processor 600 may be electrically coupled to the aforementioned biosignal sensor 100 via separate, respective conductive lines. In some example embodiments, the conductive lines may be conductive wires, conductive traces, an electrical bus, any combination thereof, or the like.

As shown, the IC and/or processor 600 may be on or at least partially embedded in a first substrate. The biosignal sensor 100 and the display region 700 may be on or at least partially embedded in a second substrate. In some example embodiments, the first and second substrates may be separate portions of a single, continuous substrate that is a single piece of material. In some example embodiments, the first and second substrates may each at least partially comprise a same material as a material included in at least a portion of the light-transmitting layer 110 as described herein. In some example embodiments at least the second substrate comprises the light-transmitting layer 110, such that the second substrate is a single piece of material having a portion thereof that is the light-transmitting layer 110 of a biosignal sensor 100.

The display region 700 may be a display panel, including an LED display panel, an OLED display panel, a liquid crystal display (LCD) panel, any combination thereof, or the like. The IC and/or processor 600 may be configured to display information on the display region 700 based on information obtains from the biosignal sensor 100.

The IC and/or processor 600 may include, may be included in, and/or may be implemented by one or more instances of processing circuitry such as hardware including logic circuits; a hardware/software combination such as a processor executing software; or any combination thereof. For example, the processing circuitry more specifically may include, but is not limited to, a central processing unit (CPU), an arithmetic logic unit (ALU), a graphics processing unit (GPU), an application processor (AP), a digital signal processor (DSP), a microcomputer, a field programmable gate array (FPGA), and programmable logic unit, a microprocessor, application-specific integrated circuit (ASIC), a neural network processing unit (NPU), an Electronic Control Unit (ECU), an Image Signal Processor (ISP), and the like. In some example embodiments, the processing circuitry may include a non-transitory computer readable storage device (e.g., memory), for example a solid state drive (SSD), storing a program of instructions, and a processor configured to execute the program of instructions to implement the functionality and/or methods performed by some or all of the IC and/or processor 600 and thus the functionality and/or methods performed by some or all of the sensor system 1000, including the functionality and/or methods performed by some or all of the biosignal sensor 100 according to any of the example embodiments.

In some example embodiments, the biosignal sensor 100 may be a skin-attachable photoplethysmography (PPG) sensor. In some example embodiments, the sensor system may be, for example, a photoplethysmography (PPG) sensor device, a functional near infrared spectroscopy (fNIRS) for brain imaging, and the like, and may be mounted on (e.g., included in) an electronic device such as a medical device or a mobile device. For example, it may be mounted on an attachable device or a wearable device.

Hereinafter, some example embodiments are illustrated in more detail with reference to examples. However, the scope of the inventive concepts is not limited these examples.

Optical Simulation

Using LightTools Software (Synopsys), the effects of the biosignal sensor according to the position of the first photo-detective element are evaluated by simulation.

The structure of the biosignal sensor is set as follows.
Biosignal sensor: photoplethysmography (PPG) sensor
Emission spectrum of the first light-emitting element: 550 nm to 650 nm ($\Delta$max=600 nm)
Assuming that internal quantum efficiency (IQE) of the first photo-detective element is 100%
Interval between the first light-emitting element and the first photo-detective element: 1 mm
Light-transmitting layer: stretchable light-transmitting layer
Thickness of light-transmitting layer: 0.05 mm
Position of the first light-emitting element (X,Y): (0,0)
Polarization direction of the first polarizer: X direction
Polarization direction of the second polarizer: Y direction
Skin composition: skin thickness 1.5 mm, blood vessel thickness 0.5 mm
The results are shown in FIGS. 17 to 19.

Figure 17:
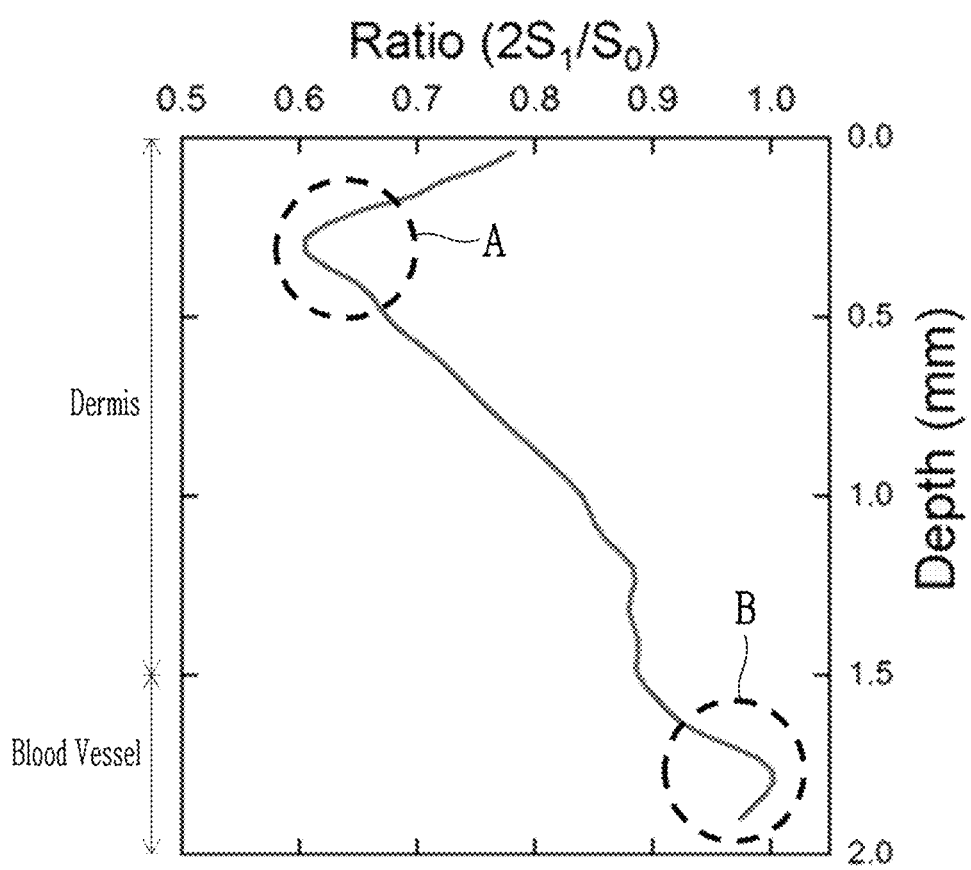
FIG. 17 is a graph showing a noise reduction effect according to a depth at which incident light reaches a living body by a second polarizer.
Figure 18:
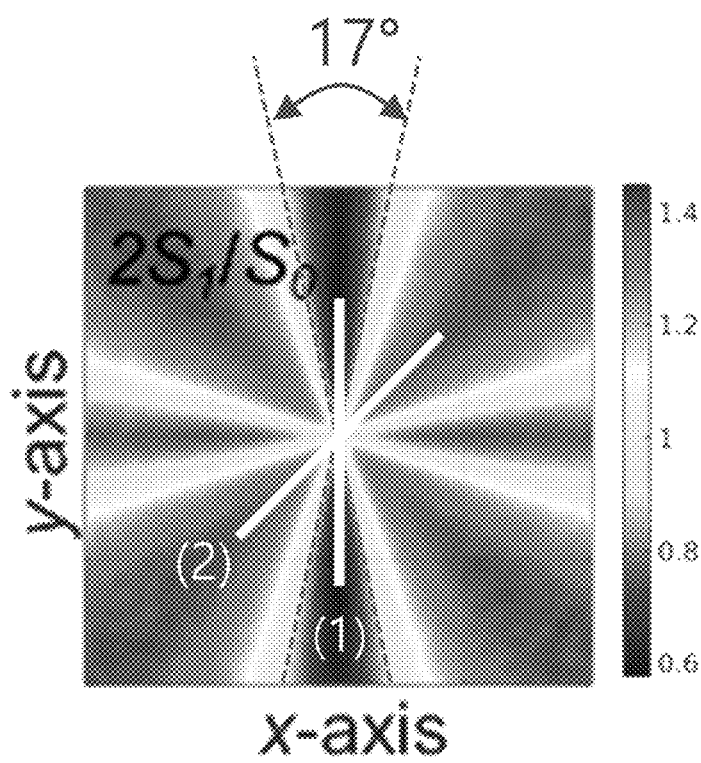
FIG. 18 is a simulation result showing $2S_1/S_0$ values according to a position on the skin plane in the portion 'A' of FIG. 17.
Figure 19:
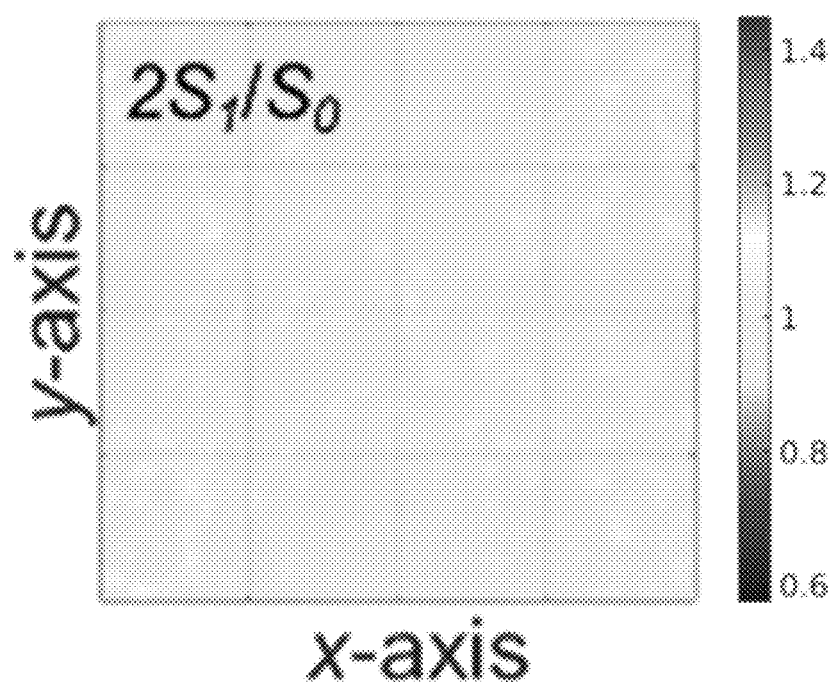
FIG. 19 is a simulation result showing $2S_1/S_0$ values according to a position on a plane in a portion 'B' of FIG. 17.

FIG. 17 is a graph showing a noise reduction effect according to a depth at which incident light reaches a living body by a second polarizer, FIG. 18 is a simulation result showing $2S_1/S_0$ values according to a position on the skin plane in the portion 'A' of FIG. 17, and FIG. 19 is a simulation result showing $2S_1/S_0$ values according to a position on a plane in a portion 'B' of FIG. 17.

Referring to FIGS. 17 to 19, about 30% to about 40% of light reflected at a depth of about 0.3 mm from the skin surface (0 mm) (a region marked by 'A', skin tissues) is removed by the second polarizer, and thus $2S_1/S_0$ is about 0.6, and a section satisfying $2S_1/S_0<1$ may be a direction (X direction or Y direction) of the first or second polarizer or within a particular (or, alternatively, predetermined) range therefrom. In other words, in FIG. 19, in a section satisfying $2S_1/S_0<1$ (light blue to strong blue section), the noise reduction effect is confirmed. On the contrary, light reflected at a depth of about 1.8 mm from the skin surface (0 mm) (a region marked by 'B' in FIG. 17, blood vessels) exhibits $2S_1/S_0$ of about 1, and regardless of locations, $2S_1/S_0$ is about 1.

EXAMPLES

Example 1

Polarization films (LPVISE 2×2, Thorlab, Inc.) are attached to each lower portion of a light-emitting element and a photo-detective element of a PPG module (OSRAM SFH7060) to manufacture a patch-type (fixed-type) biosignal sensor. Herein, a polarization direction of the polarization film attached to the lower portion of the light-emitting element is perpendicular to a polarization direction of the polarization film attached to the lower portion of the photo-detective element.

Example 2

A biosignal sensor is manufactured in the same method as Example 1 except that a band-type (non-fixed type) biosignal sensor is adopted instead of the patch type biosignal sensor.

Reference Example 1

A PPG module (OSRAM SFH7060) is prepared as a patch-type (fixed-type) biosignal sensor where no polarization film is attached.

Reference Example 2

A biosignal sensor is manufactured in the same method as in Reference Example 1 except that a band-type (non-fixed type) biosignal sensor is adopted instead of the patch-type biosignal sensor.
Evaluation I After respectively attaching the patch-type biosignal sensors according to Example 1 and Reference Example 1 on a wrist and wearing the band-type biosignal sensors according to Example 2 and Reference Example 2 on a wrist, PPG signals are measured while the wrist is repeatedly bent inward ($-\alpha°$)-outward ($+\alpha°$) at 0.5 Hz cycles. The measured PPG signals are Fourier-transformed (FT) to express a ratio of intensities of 0.5 Hz component (motion artifacts) and 1.1 Hz component (PPG signals).

Figure 20:
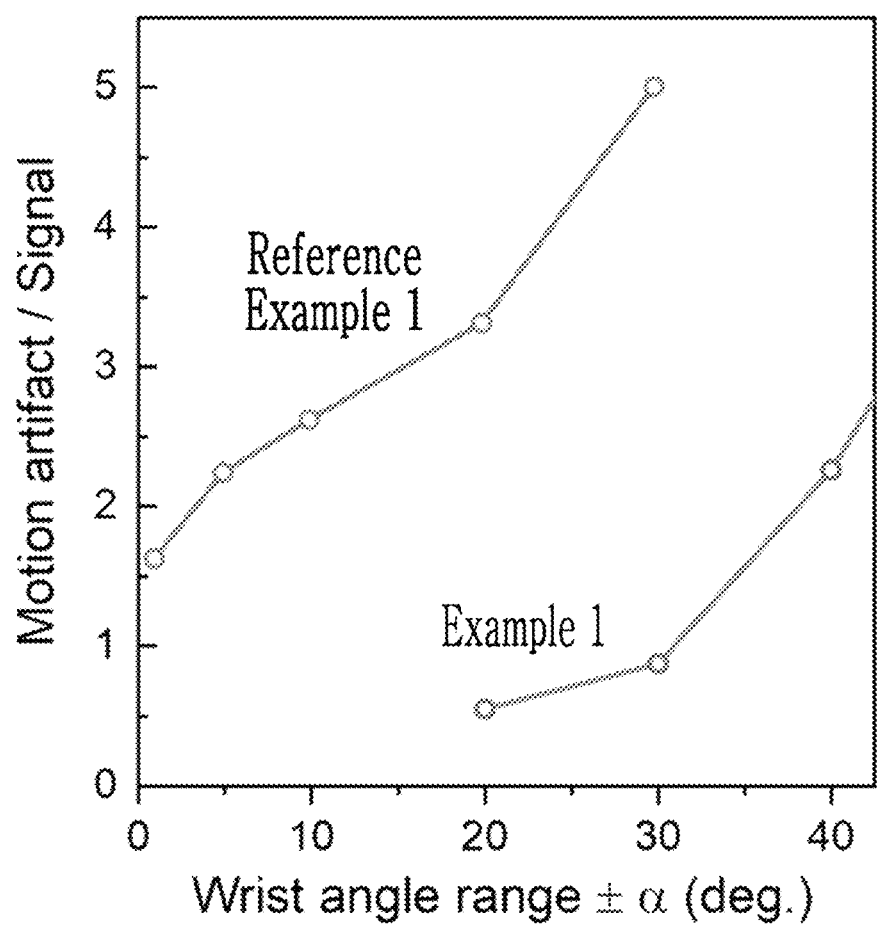
FIG. 20 is a graph showing ratios of signal intensities according to motions of the biosignal sensors according to Example 1 and Reference Example 1.
Figure 21:
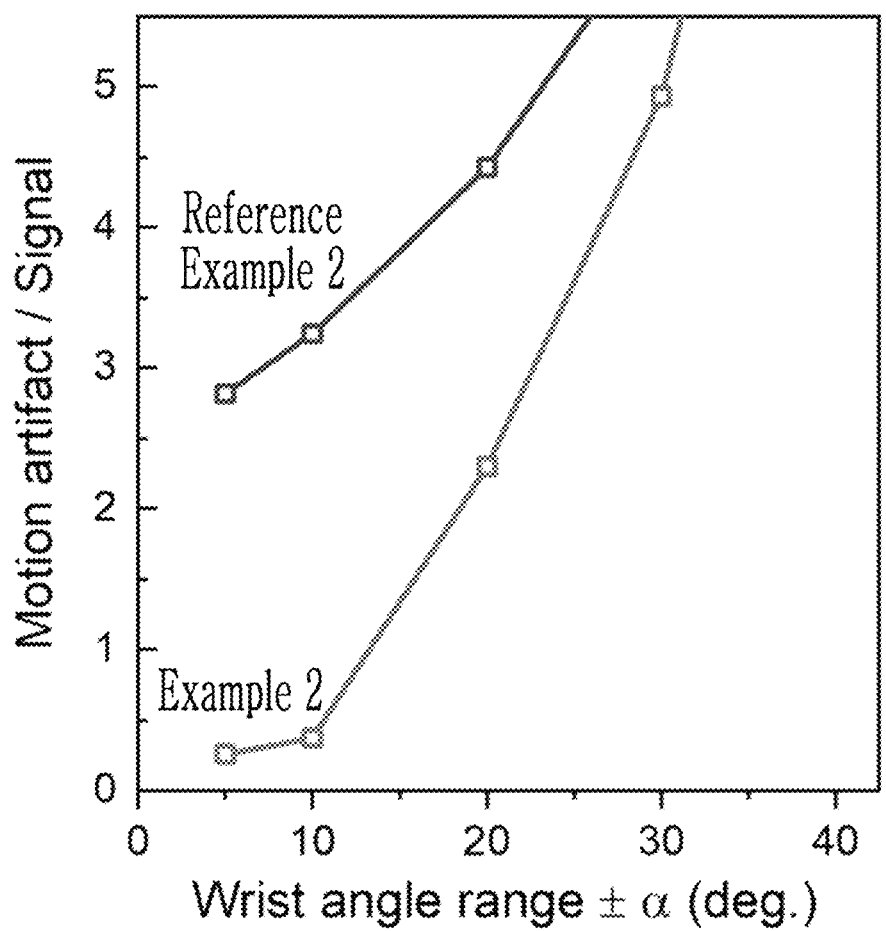
FIG. 21 is a graph showing ratios of signal intensities according to motions of the biosignal sensors according to Example 2 and Reference Example 2.

The results are shown in FIGS. 20 and 21.

FIG. 20 is a graph showing ratios of signal intensities according to motions of the biosignal sensors according to Example 1 and Reference Example 1, and FIG. 21 is a graph showing ratios of signal intensities according to motions of biosignal sensors according to Example 2 and Reference Example 2.

Referring to FIG. 20, the patch-type biosignal sensor according to Example 1 exhibit low noises depending on a degree of motion (an angle at which the wrist is bent), compared with the patch-type biosignal sensor according to Reference Example 1. Likewise, referring to FIG. 21, the band-type biosignal sensor according to Example 2 exhibits low noises depending on a degree of motion, compared with the band-type biosignal sensor according to Reference Example 2.
Evaluation II After respectively attaching the patch-type biosignal sensors according to Example 1 and Reference Example 1 on a wrist and wearing the biosignal sensors according to Example 2 and Reference Example 2 on a wrist, PPG signals and FFT spectra are evaluated while the wrist is repeatedly bent inward (−20°)-outward (+20°) at 0.5 Hz cycles.

The results are shown in FIGS. 22 to 25.

Figure 22:
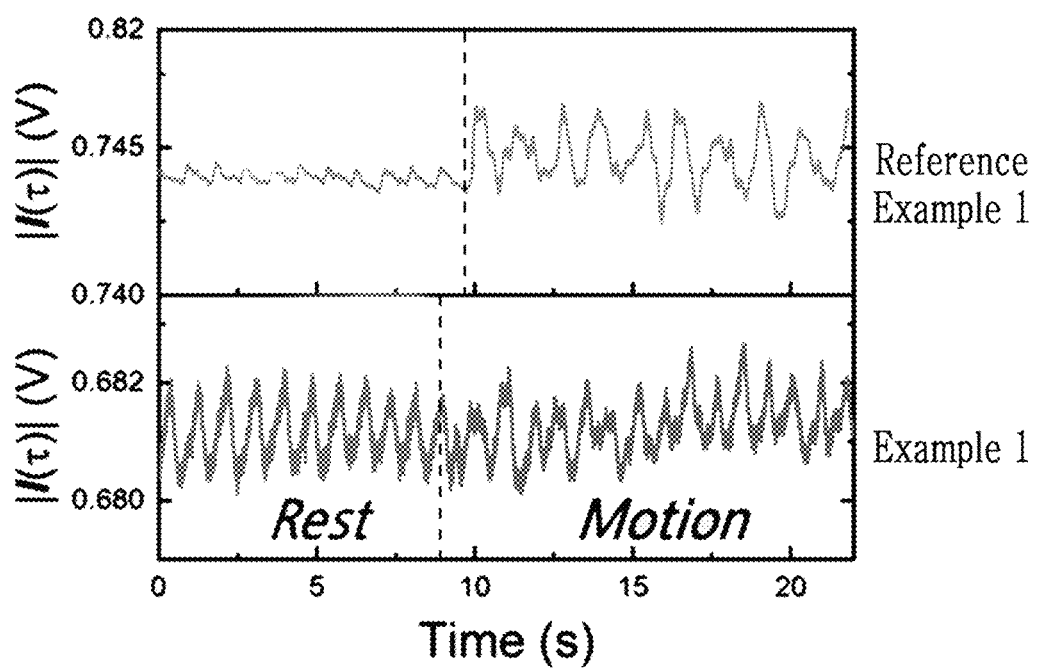
FIG. 22 is a graph showing biosignal changes of the biosignal sensors according to Example 1 and Reference Example 1 in a resting state (stop state) and an exercise state (motion state)
Figure 23:
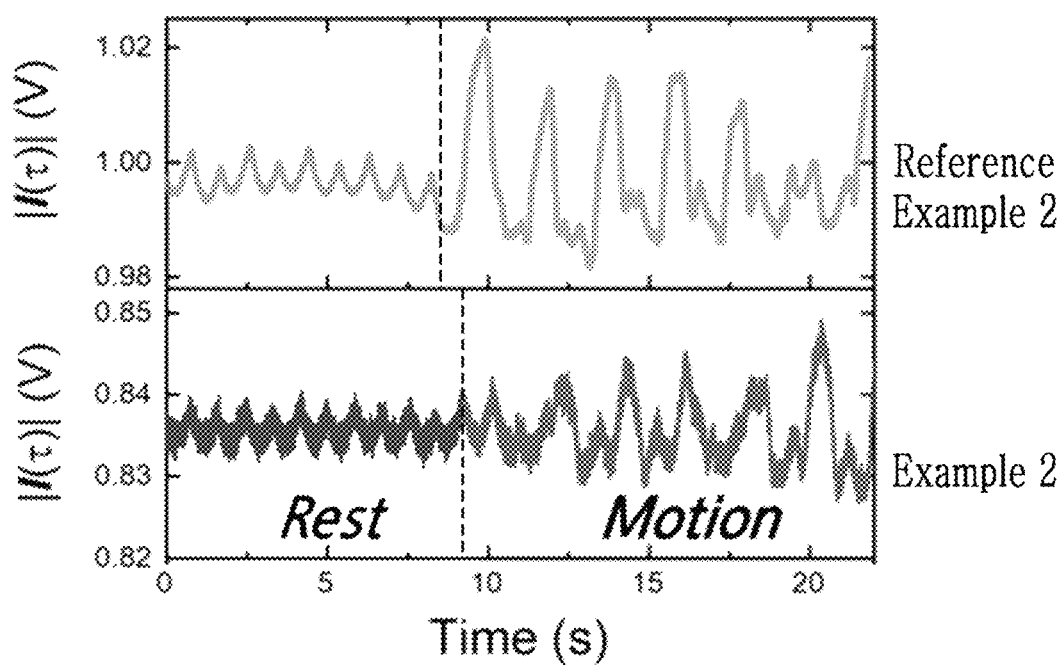
FIG. 23 is a graph showing biosignal changes of the biosignal sensors according to Example 2 and Reference Example 2 in a resting state (stop state) and an exercise state (motion state)
Figure 24:
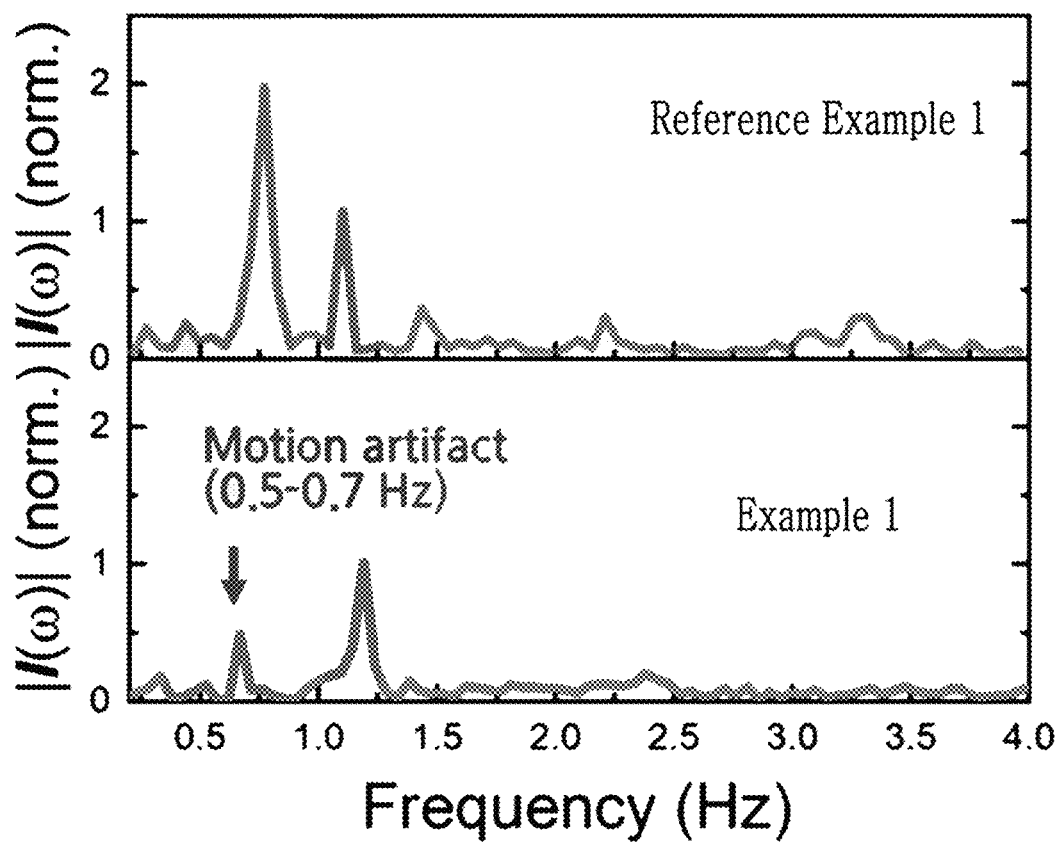
FIG. 24 shows FFT spectra of the biosignal sensors according to Example 1 and Reference Example 1.
Figure 25:
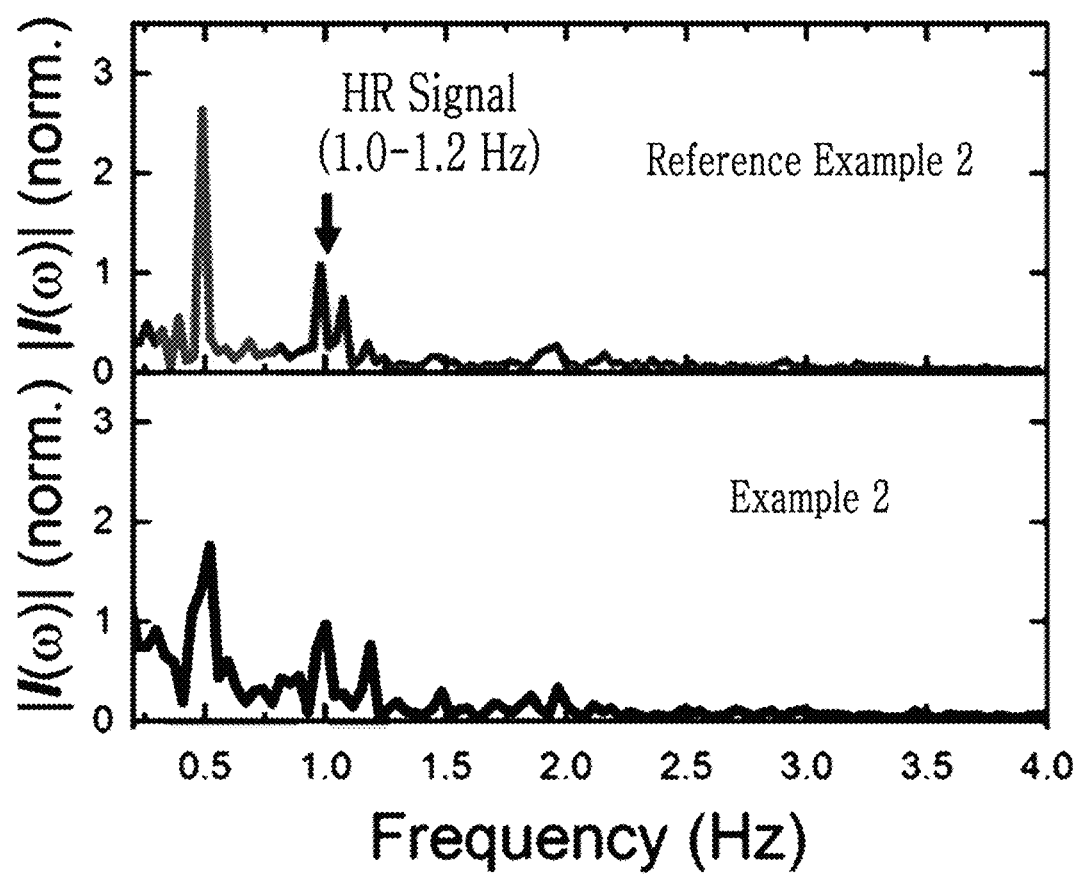
FIG. 25 shows FFT spectra of a biosignal sensor according to Example 2 and Reference Example 2.

FIG. 22 is a graph showing biosignal changes of the biosignal sensors according to Example 1 and Reference Example 1 for a rest (stop state) and an exercise (motion state), FIG. 23 is a graph showing biosignal changes of the biosignal sensors according to Example 2 and Reference Example 2 for a rest (stop state) and an exercise (motion state), FIG. 24 shows FFT spectra expressed as a frequency by Fourier transforming the biosignal sensors according to Example 1 and Reference Example 1 in an exercise (motion state), and FIG. 25 shows FFT spectra expressed as a frequency by Fourier transforming the biosignal sensor according to Example 2 in an exercise (motion state).

Referring to FIGS. 22 and 23, the biosignal sensors according to Examples 1 and 2 exhibit relatively small noises during the motions, respectively, compared with the biosignal sensors according to Reference Examples 1 and 2, and accordingly, the motions have different influences depending on the presence or absence of a polarizer.

Referring to FIG. 24, comparing intensity of motion noise (motion artifact) at a frequency of about 0.5 Hz (about 0.5 to 0.7 Hz) with that of heart rate signal (HR signal) at a frequency of about 1 Hz (about 1 to 1.2 Hz), the biosignal sensor according to Example 1 exhibits smaller noise (motion artifact) than the heart rate signal, but the biosignal sensor according to Reference Example 1 exhibits larger motion noise than the heart rate signal.

Referring to FIG. 25, comparing intensity of motion noise (motion artifact) at a frequency of about 0.5 Hz (about 0.5 to 0.7 Hz) with that of heart rate signal (HR signal) at a frequency about 1 Hz (about 1 to 1.2 Hz), the biosignal sensor according to Example 2 exhibits a lower ratio of noise to heart signal.

While the inventive concepts have been described in connection with what is presently considered to be practical example embodiments, it is to be understood that the inventive concepts are not limited to these example embodiments. On the contrary, the inventive concepts are intended to cover various modifications and equivalent arrangements included within the spirit and scope of the appended claims.

What is claimed is:

1. A biosignal sensor, comprising:
a light-transmitting layer;
a light-emitting element;
a photo-detective element configured to detect a biosignal from light reflected from a target that is external to the biosignal sensor;
a first polarizer configured to selectively transmit light in a first polarization direction; and
a second polarizer configured to selectively transmit light in a second polarization direction,
wherein the light-emitting element includes a first light-emitting element overlapped with the first polarizer in a thickness direction of the light-transmitting layer,
wherein the photo-detective element includes a first photo-detective element overlapped with the second polarizer in the thickness direction of the light-transmitting layer,
wherein the first light-emitting element and the first photo-detective element are arranged to be parallel to each other along a first direction that is perpendicular to the thickness direction of the light-transmitting layer, and
wherein the first polarization direction and the second polarization direction are perpendicular to each other, and
wherein an angle of the first polarization direction or the second polarization direction with respect to the first direction satisfies Relationship Equation 1, $$2S_1/S_0 < 1.0 \qquad \text{[Relationship Equation 1]}$$

wherein, in Relationship Equation 1,
$S_1$ is an amount of light measured by the first photo-detective element when the angle of the first polarization direction or the second polarization direction with respect to the first direction is θ degrees, and $S_O$ is an amount of light measured by the first photo-detective element when the light measured by the first photo-detective element is not polarized in at least the second polarization direction.

2. The biosignal sensor of claim 1, wherein the angle of the first polarization direction or the second polarization direction with respect to the first direction is in a range of about −8.5 degrees to about +8.5 degrees.

3. The biosignal sensor of claim 2, wherein the first polarization direction or the second polarization direction is parallel to the first direction.

4. The biosignal sensor of claim 1, wherein
the first polarization direction is parallel to the first direction and the second polarization direction is perpendicular to the first direction, or
the second polarization direction is parallel to the first direction and the first polarization direction is perpendicular to the first direction.

5. The biosignal sensor of claim 1, wherein
the photo-detective element includes a plurality of first photo-detective elements, the plurality of first photo-detective elements including the first photo-detective element, and
some first photo-detective elements of the plurality of first photo-detective elements are at opposite sides of the first light-emitting element along the first direction.

6. The biosignal sensor of claim 5, wherein some other first photo-detective elements of the plurality of first photo-detective elements are at opposite sides of the first light-emitting element along a second direction that is perpendicular to both the first direction and the thickness direction of the light-transmitting layer.

7. The biosignal sensor of claim 1, wherein the photo-detective element further comprises a second photo-detective element, the second photo-detective element being not overlapped with the second polarizer in the thickness direction of the light-transmitting layer.

8. The biosignal sensor of claim 7, wherein the first light-emitting element and the second photo-detective element are parallel to each other along a third direction, the third direction being not parallel or perpendicular to the first direction.

9. The biosignal sensor of claim 7, wherein the light-emitting element further includes a second light-emitting element, the second light-emitting element being not overlapped with the first polarizer in the thickness direction of the light-transmitting layer.

10. The biosignal sensor of claim 9, wherein
the photo-detective element includes a plurality of first photo-detective elements, the plurality of first photo-detective elements including the first photo-detective element,
the photo-detective element includes a plurality of second photo-detective elements, the plurality of second photo-detective elements including the second photo-detective element,
wherein some first photo-detective elements of the plurality of first photo-detective elements are at one or opposite sides of the first light-emitting element along the first direction,
wherein some other first photo-detective elements of the plurality of first photo-detective elements are at one or opposite sides of the first light-emitting element along a second direction that is perpendicular to the first direction and the thickness direction of the light-transmitting layer,
some second photo-detective elements of the plurality of second photo-detective elements are at one or opposite sides of the first light-emitting element along a third direction, the third direction being different from the first direction and the second direction and perpendicular to the thickness direction of the light-transmitting layer, and
some other second photo-detective elements of the plurality of second photo-detective elements are at one or opposite sides of the first light-emitting element along a fourth direction, the fourth direction being different from the first direction, the second direction, and the third direction and perpendicular to the thickness direction of the light-transmitting layer.

11. The biosignal sensor of claim 1, further comprising a phase retarder between the first light-emitting element and the first polarizer.

12. The biosignal sensor of claim 1, wherein the biosignal sensor is a skin-attachable photoplethysmography (PPG) sensor.

13. A biosignal sensor, comprising:
a first biosignal sensor including a light-transmitting layer, a first photo-detective element and a first polarizer that is overlapped with the first photo-detective element in a thickness direction of the light-transmitting layer, the first polarizer configured to selectively transmit light in a first polarization direction, the first photo-detective element configured to detect a biosignal from light reflected from a target that is external to the first biosignal sensor; and
a second biosignal sensor including a second photo-detective element that does not overlap with any polarizers in the thickness direction of the light-transmitting layer,
wherein the first biosignal sensor and the second biosignal sensor are configured to operate independently, and
wherein an angle of the first polarization direction with respect to a first direction that is perpendicular to the thickness direction of the light-transmitting layer satisfies Relationship Equation 1, $$2S_1/S_0<1.0 \qquad \text{[Relationship Equation 1]}$$

wherein, in Relationship Equation 1,
$S_1$ is an amount of light measured by the first photo-detective element when the angle of the first polarization direction with respect to the first direction is θ degrees, and
$S_O$ is an amount of light measured by the first photo-detective element when the light measured by the first photo-detective element is not polarized in at least the first polarization direction.

14. The biosignal sensor of claim 13, further comprising a first light-emitting element that is overlapped with a second polarizer in the thickness direction of the light-transmitting layer.

15. The biosignal sensor of claim 14, wherein
the biosignal sensor includes a plurality of first biosignal sensors, the plurality of first biosignal sensors including the first biosignal sensor,
wherein some first biosignal sensors of the plurality of first biosignal sensors are at one or opposite sides of the first light-emitting element along the first direction that is perpendicular to the thickness direction of the light-transmitting layer, and some other first biosignal sensors of the plurality of first biosignal sensors are at one or opposite sides of the first light-emitting element along a second direction, the second direction being perpendicular to both the first direction and the thickness direction of the light-transmitting layer.

16. The biosignal sensor of claim 15, wherein
the biosignal sensor includes a plurality of second biosignal sensors, the plurality of second biosignal sensors including the second biosignal sensor,
wherein some second biosignal sensors of the plurality of the second biosignal sensors are at one or opposite sides of the first light-emitting element along a third direction, the third direction being different from both the first direction and the second direction and perpendicular to the thickness direction of the light-transmitting layer, and
some other second biosignal sensors of the plurality of the second biosignal sensors are at one or opposite sides of the first light-emitting element along a fourth direction, the fourth direction being different from the first direction, the second direction, and the third direction and perpendicular to the thickness direction of the light-transmitting layer.

17. The biosignal sensor of claim 13, further comprising a light-emitting element.

18. The biosignal sensor of claim 17, wherein the light-emitting element comprises a first light-emitting element that is overlapped with a second polarizer in the thickness direction of the light-transmitting layer.

19. The biosignal sensor of claim 13, wherein
the first biosignal sensor further includes a first light-emitting element that is overlapped with a second polarizer in the thickness direction of the light-transmitting layer, and
the second biosignal sensor further includes a second light-emitting element that does not overlap with any polarizers in the thickness direction of the light-transmitting layer.

20. The biosignal sensor of claim 19, wherein the first biosignal sensor further includes a phase retarder.

21. The biosignal sensor of claim 13, wherein the biosignal sensor is a skin-attachable photoplethysmography (PPG) sensor.

22. A sensor system, the sensor system comprising the biosignal sensor of claim 1, and an integrated circuit or a processor for processing a biosignal obtained from the biosignal sensor.

23. The sensor system of claim 22, further comprising a motion detecting sensor.

24. An electronic device comprising the biosignal sensor of claim 1, the electronic device being an attachable or wearable device.

25. A method of operating the biosignal sensor of claim 13, the method comprising:
detecting a motion of an attachment or wearing portion of a user;
selectively driving the first biosignal sensor or the second biosignal sensor according to the detected motion; and
obtaining a biosignal from the first biosignal sensor or the second biosignal sensor.

26. The method of claim 25, wherein
the selectively driving of the first biosignal sensor or the second biosignal sensor comprises
selectively driving the first biosignal sensor in response to the motion of the attachment or wearing portion of the user being detected, and
selectively driving the second biosignal sensor in response to the motion of the attachment or wearing portion of the user not being detected.

* * * * *